United States Patent
Jegannathan et al.

(10) Patent No.: US 12,293,845 B2
(45) Date of Patent: May 6, 2025

(54) AI DRIVEN SMART PATIENT LABELING SYSTEM

(71) Applicant: International Business Machines Corporation, Armonk, NY (US)

(72) Inventors: Saigeetha Aswathnarayanan Jegannathan, Bangalore (IN); Sridhar Jonnala, Bangalore (IN); V Datta Kamesam Jami, Srikakulam (IN); Chinthalapudi Venkata Sai Vishnu Vardhan, Kandukur (IN); Naman Mathur, Jaipur (IN); Shivangi Tak, Gurgaon (IN); Kartikeya Vats, Dehradun (IN)

(73) Assignee: International Business Machines Corporation, Armonk, NY (US)

( * ) Notice: Subject to any disclaimer, the term of this patent is extended or adjusted under 35 U.S.C. 154(b) by 450 days.

(21) Appl. No.: 17/809,416

(22) Filed: Jun. 28, 2022

(65) Prior Publication Data
US 2023/0420146 A1    Dec. 28, 2023

(51) Int. Cl.
G06F 17/00    (2019.01)
G06F 40/289    (2020.01)
G06F 40/40    (2020.01)
G06N 5/022    (2023.01)
G16H 70/40    (2018.01)

(52) U.S. Cl.
CPC .......... *G16H 70/40* (2018.01); *G06F 40/289* (2020.01); *G06F 40/40* (2020.01); *G06N 5/022* (2013.01)

(58) Field of Classification Search
None
See application file for complete search history.

(56) References Cited

U.S. PATENT DOCUMENTS

| | | | |
|---|---|---|---|
| 7,035,877 B2 | 4/2006 | Markham | |
| 7,912,700 B2 | 3/2011 | Bower | |
| 8,583,457 B1 * | 11/2013 | Lewis | G16H 20/10 |
| | | | 707/769 |
| 8,694,555 B2 | 4/2014 | Gogolak | |

(Continued)

OTHER PUBLICATIONS

Ahmed et al., "A Generic Method for Automatic Ground Truth Generation of Camera-captured Documents", arXiv:1605.01189v1 [cs.CV], May 4, 2016, 15 Pages.
Balon et al., "Design of a computer program for automatic capture of adverse drug interaction and contraindication data detected during prescription labelling", International Journal of Pharmacy Practice, vol. 5, Issue 2, Jun. 1997, 6 Pages.

(Continued)

*Primary Examiner* — Satwant K Singh
(74) *Attorney, Agent, or Firm* — Monchai Chuaychoo

(57) ABSTRACT

In an approach for automatically identifying one or more updates in a Scientific Drug Label (SL) relevant to a patient and incorporating the one or more updates into a Patient Drug Label (PL), a processor receives a pair of documents, wherein the pair of documents include the SL and the PL. A processor converts a complex medical language of the SL into a simplified patient friendly language. A processor identifies one or more words, one or more phrases, or one or more sentences that have been modified, inserted, or deleted. A processor searches for a location in the PL that closely maps to the one or more words, the one or more phrases, or the one or more sentences to the SL. A processor incorporates the one or more words, the one or more phrases, or the one or more sentences in a mapped location of the PL.

16 Claims, 11 Drawing Sheets

(56) References Cited

U.S. PATENT DOCUMENTS

| | | | |
|---|---|---|---|
| 11,011,254 B2* | 5/2021 | Martin | G06F 16/316 |
| 2012/0209625 A1 | 8/2012 | Armstrong | |
| 2014/0136229 A1 | 5/2014 | Levine | |
| 2014/0222448 A1 | 8/2014 | Janson | |
| 2019/0188562 A1* | 6/2019 | Edwards | G06N 5/045 |
| 2020/0272857 A1 | 8/2020 | Arcot Desai | |
| 2021/0295955 A1 | 9/2021 | Lee | |

OTHER PUBLICATIONS

Esplà-Gomis et al., "Predicting insertion positions in word-level machine translation quality estimation", Applied Soft Computing, vol. 76, Mar. 2019, 3 Pages. (Abstract Only).

Graus et al., "Generating Pseudo-ground Truth for Predicting New Concepts in Social Streams", ECIR 2014: Proceedings of the 36th European Conference on IR Research on Advances in Information Retrieval, vol. 8416, Apr. 2014, 13 Pages.

Liang et al., "Ground Truth Creation for Complex Clinical NLP Tasks—an Iterative Vetting Approach and Lessons Learned", Proceedings—AMIA Joint Summits on Translational Science, 2017, 10 Pages.

Loftware, "New survey reveals the importance of standardized label management in pharmaceutical industry", Loftware, NiceLabel, Jun. 27, 2017, 5 Pages.

U.S. Food & Drug Administration, "Prescription Drug Labeling Resources", U.S. Food & Drug Administration, Oct. 7, 2021, 18 Pages.

* cited by examiner

AI DRIVEN SMART PATIENT LABELING SYSTEM

BACKGROUND OF THE INVENTION

The present invention relates generally to the field of data processing, and more particularly to an artificially intelligent driven smart patient labeling system.

The Food and Drug Administration (FDA) is responsible for determining whether a pharmaceutical drug is safe and effective for use under the conditions prescribed, recommended, or suggested in a proposed labeling. Once a pharmaceutical drug is approved, the FDA requires labeling that sets forth the conditions of use under which the pharmaceutical drug has been shown to meet the relevant standard for marketing. The FDA-required labeling also provides directions and information on how to use the pharmaceutical drug safely and effectively.

For every pharmaceutical drug, there are two labels generated: a Scientific Drug Label and a Patient Drug Label. A Scientific Drug Label is meant for the medical practitioners who prescribe the pharmaceutical drug to patients. The Scientific Drug Label is complex as it contains scientific terms and medical terminology. The Scientific Drug Label contains information relevant to the medical practitioner such as a name of the pharmaceutical drug, a composition of the pharmaceutical drug, a shape and/or appearance of the pharmaceutical drug, and a medical condition treated by the pharmaceutical drug. A Patient Drug Label is meant for the patients who are prescribed the pharmaceutical drug. The Patient Drug Label has simpler language and is devoid of complex medical terms. The Patient Drug Label contains information relevant to the patient such as a method to administer the pharmaceutical drug, one or more side effects a patient may experience when taking the pharmaceutical drug, and one or more precautions a patient should take when using the pharmaceutical drug.

SUMMARY

Aspects of an embodiment of the present invention disclose a method, computer program product, and computer system for automatically identifying one or more updates in a Scientific Drug Label relevant to a patient and incorporating the one or more updates into a Patient Drug Label. A processor receives a pair of documents from a user, wherein the pair of documents include a Scientific Drug Label and a Patient Drug Label. A processor converts a complex medical language of the Scientific Drug Label into a simplified patient friendly language. A processor analyzes the simplified patient friendly language to identify one or more words, one or more phrases, or one or more sentences that have been modified, inserted, or deleted. Responsive to determining the one or more words, the one or more phrases, or the one or more sentences are relevant to a patient, a processor classifies the one or more words, the one or more phrases, or the one or more sentences in one or more categories. A processor searches for a location in the Patient Drug Label that closely maps to the one or more words, the one or more phrases, or the one or more sentences to the Scientific Drug Label. A processor incorporates the one or more words, the one or more phrases, or the one or more sentences in a mapped location of the Patient Drug Label. A processor outputs an updated Patient Drug Label to the user.

In some aspects of an embodiment of the present invention, the one or more categories include a complete insertion of a sentence in the Scientific Drug Label, a complete deletion of the sentence in the Scientific Drug Label, and an insertion or a deletion of a word or a phrase in the Scientific Drug Label.

In some aspects of an embodiment of the present invention, subsequent to outputting the updated Patient Drug Label to the user, a processor requests feedback from the user. Responsive to receiving the feedback from the user, a processor validates the feedback received from the user manually using a confidence score of one or more intermediate outputs. A processor annotates the feedback received from the user.

In some aspects of an embodiment of the present invention, subsequent to annotating the feedback received from the user, a processor identifies one or more engines to be retrained. A processor retrains the one or more engines with the annotated feedback.

In some aspects of an embodiment of the present invention, the feedback received from the user includes an acceptance or a rejection of the one or more changes incorporated into the updated Patient Drug Label.

In some aspects of an embodiment of the present invention, a processor converts the pair of documents from a word format to a Portable Document Format (PDF). A processor extracts content from the PDF of the Scientific Drug Label in a structured format. A processor sorts the extracted content into a corresponding section heading or a corresponding section subheading.

In some aspects of an embodiment of the present invention, subsequent to sorting the extracted content into the corresponding section heading or the corresponding section subheading, a processor extracts one or more keywords and one or more key phrases from the extracted content using a custom-trained Spacey model to understand a concept of each sentence of the extracted content. A processor maps one or more relationships between the Scientific Drug Label and the Patient Drug Label using a knowledge graph. A processor extracts a confidence score for the one or more relationships mapped between the Scientific Drug Label and the Patient Drug Label.

In some aspects of an embodiment of the present invention, the one or more keywords and the one or more key phrases extracted from the structured data includes a name of a drug, a composition of the drug, a shape of the drug, an appearance of the drug, a medical condition treated by the drug, a method to administer the drug, one or more side effects the patient may experience when taking the drug, and one or more precautions the patient should take when using the drug.

In some aspects of an embodiment of the present invention, a processor generates a model for the one or more keywords and the one or more key phrases from the extracted content. A processor determines a position of the one or more keywords and the one or more key phrases from the extracted content. A processor annotates the position of the one or more keywords and the one or more key phrases from the extracted content. A processor trains on the annotated position of the one or more keywords and the one or more key phrases.

In some aspects of an embodiment of the present invention, a processor modifies the one or more words, the one or more phrases, or the one or more sentences in the mapped location of the Patient Drug Label.

In some aspects of an embodiment of the present invention, a processor inserts the one or more words, the one or more phrases, or the one or more sentences in the mapped location of the Patient Drug Label.

In some aspects of an embodiment of the present invention, a processor deletes the one or more words, the one or more phrases, or the one or more sentences in the mapped location of the Patient Drug Label.

These and other features and advantages of the present invention will be described in, or will become apparent to those of ordinary skill in the art in view of, the following detailed description of the example embodiments of the present invention.

DETAILED DESCRIPTION

Figure 1:
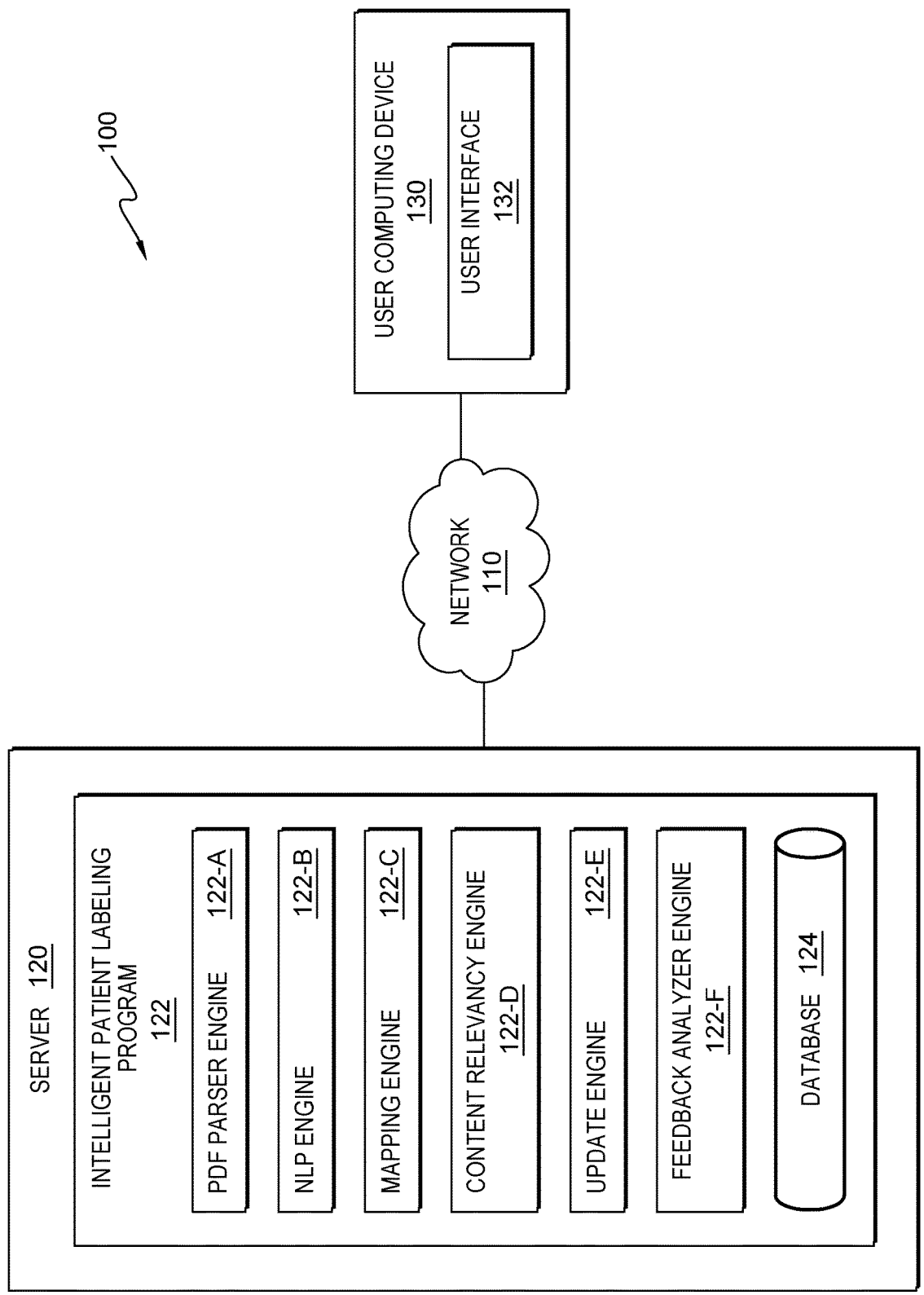
FIG. 1 is a block diagram illustrating a distributed data processing environment, in accordance with an embodiment of the present invention.

Embodiments of the present invention recognize that the Food and Drug Administration (FDA) determines whether a pharmaceutical drug is safe and effective for use under the conditions prescribed, recommended, or suggested in a proposed labeling submitted with the pharmaceutical drug's marketing application. In making this determination, the FDA evaluates whether the conditions of use in the proposed labeling are supported by the required levels and types of evidence of safety and effectiveness and whether the benefits of using the pharmaceutical drug under those specific conditions of use outweigh the risks of the pharmaceutical drug.

Embodiments of the present invention recognize that, after the FDA approves or clears a pharmaceutical drug, the FDA requires labeling that sets forth the conditions of use under which the pharmaceutical drug has been shown to meet the relevant standard for marketing. The FDA-required labeling also provides directions and information on how to use the pharmaceutical drug safely and effectively. The FDA-required labeling is the primary tool that communicates the essential information needed for the safe and effective use of the pharmaceutical drug by the user (i.e., a medical practitioner and a patient), and companies have an obligation to update their FDA-required labeling as needed to ensure it is not false or misleading. The essential information may include, but is not limited to, a name of the pharmaceutical drug, a composition of the pharmaceutical drug (i.e., the ingredients of the pharmaceutical drug and the concentration of the ingredients), a shape and/or appearance of the pharmaceutical drug, a medical condition treated by the pharmaceutical drug, a method to administer the pharmaceutical drug, one or more side effects a patient may experience when taking the pharmaceutical drug (i.e., one or more unwanted or unexpected symptoms or feelings that may occur when taking the pharmaceutical drug), and one or more precautions a patient should take when using the pharmaceutical drug. However, a label is not intended to exhaustively address all that is known about the pharmaceutical drug for its approved or cleared uses.

Embodiments of the present invention recognize that providing the FDA-required labeling is a critical step in maintaining compliance for a pharmaceutical drug that is released to the market. For every pharmaceutical drug, there are two labels generated: a Scientific Drug Label and a Patient Drug Label. A Scientific Drug Label is meant for the medical practitioners who prescribe the pharmaceutical drug to patients. The Scientific Drug Label is complex as it contains scientific terms and medical terminology. The Scientific Drug Label contains information relevant to the medical practitioner such as a name of the pharmaceutical drug, a composition of the pharmaceutical drug, a shape and/or appearance of the pharmaceutical drug, and a medical condition treated by the pharmaceutical drug. A Patient Drug Label is meant for the patients who are prescribed the pharmaceutical drug. The Patient Drug Label has simpler language and is devoid of complex medical terms. The Patient Drug Label contains information relevant to the patient such as a method to administer the pharmaceutical drug, one or more side effects a patient may experience when taking the pharmaceutical drug, and one or more precautions a patient should take when using the pharmaceutical drug.

Embodiments of the present invention recognize that simplification of the technical information of a pharmaceutical drug into patient friendly language requires a great deal of manual intervention, especially when there are updates in the Scientific Drug Label that need to be incorporated into the Patient Drug Label. Typically, pharmaceutical and biopharmaceutical companies employ a group of Subject Matter Experts (SMEs) who generate the Patient Drug Label when a new pharmaceutical drug is released to the market and who update the Patient Drug Label when a pharmaceutical drug currently on the market is changed in some way. Currently, the SMEs for the pharmaceutical and biopharmaceutical companies must manually check for updates and must determine whether the update is relevant to the patient and, therefore, should be incorporated into the Patient Drug Label. The SMEs determination of relevancy is based on the SME's knowledge. When the update is deemed relevant to the patient, the SMEs must incorporate the update into the Patient Drug Label manually. This process, however, is not a straightforward process and requires multiple rounds of verification and approval before the Patient Drug Label is updated and released to the public. Therefore, this process can be time consuming. Embodiments of the present invention recognize the need for a system and method to mitigate the potential ineffectiveness of manual updates of Patient Drug Labels.

Embodiments of the present invention provide a system and method to automatically identify one or more updates in a Scientific Drug Label that are relevant to a patient; to identify what type of update (i.e., insert, delete, modify) each of the one or more updates in the Scientific Drug Label are and where (i.e., appropriate position) each of the one or more updates needs to be incorporated into a Patient Drug Label; to transform the complex medical language of the update into simple patient learning language without losing contextual information; to incorporate each of the one or more updates into the Patient Drug Label; and to analyze user feedback data and separate the feedback based on engines to be retrained using an intelligent data annotator for the respective engines training.

Implementation of embodiments of the present invention may take a variety of forms, and exemplary implementation details are discussed subsequently with reference to the Figures.

FIG. 1 is a block diagram illustrating a distributed data processing environment, generally designated 100, in accordance with an embodiment of the present invention. In the depicted embodiment, distributed data processing environment 100 includes server 120 and user computing device 130, interconnected over network 110. Distributed data processing environment 100 may include additional servers, computers, computing devices, and other devices not shown. The term "distributed" as used herein describes a computer system that includes multiple, physically distinct devices that operate together as a single computer system. FIG. 1 provides only an illustration of one embodiment of the present invention and does not imply any limitations with regards to the environments in which different embodiments may be implemented. Many modifications to the depicted environment may be made by those skilled in the art without departing from the scope of the invention as recited by the claims.

Network 110 operates as a computing network that can be, for example, a telecommunications network, a local area network (LAN), a wide area network (WAN), such as the Internet, or a combination of the three, and can include wired, wireless, or fiber optic connections. Network 110 can include one or more wired and/or wireless networks capable of receiving and transmitting data, voice, and/or video signals, including multimedia signals that include data, voice, and video information. In general, network 110 can be any combination of connections and protocols that will support communications between server 120, user computing device 130, and other computing devices (not shown) within distributed data processing environment 100.

Server 120 operates to run intelligent patient labeling program 122 and to send and/or store data in database 124. In an embodiment, server 120 can send data from database 124 to user computing device 130. In an embodiment, server 120 can receive data in database 124 from user computing device 130. In one or more embodiments, server 120 can be a standalone computing device, a management server, a web server, a mobile computing device, or any other electronic device or computing system capable of receiving, sending, and processing data and capable of communicating with user computing device 130 via network 110. In one or more embodiments, server 120 can be a computing system utilizing clustered computers and components (e.g., database server computers, application server computers, etc.) that act as a single pool of seamless resources when accessed within distributed data processing environment 100. In one or more embodiments, server 120 can be a laptop computer, a tablet computer, a netbook computer, a personal computer, a desktop computer, a personal digital assistant, a smart phone, or any programmable electronic device capable of communicating with user computing device 130 and other computing devices (not shown) within distributed data processing environment 100 via network 110. Server 120 may include internal and external hardware components, as depicted and described in further detail in FIG. 11.

Intelligent patient labeling program 122 operates to automatically identify one or more updates in a Scientific Drug Label relevant to a patient; to identify the type of update and the appropriate position of the update in a Patient Drug Label; to transform the complex medical language of the update into simple patient learning language without losing contextual information; and to incorporate the update into the Patient Drug Label. In the depicted embodiment, intelligent patient labeling program 122 is a standalone program. In another embodiment, intelligent patient labeling program 122 may be integrated into another software product, such as a pharmaceutical labeling software. In the depicted embodiment, intelligent patient labeling program 122 resides on server 120. In another embodiment, intelligent patient labeling program 122 may reside on user computing device 130 or on another computing device (not shown), provided that intelligent patient labeling program 122 has access to network 110. In the depicted embodiment, intelligent patient labeling program 122 includes PDF Parser Engine 122-A, Natural Language Processing (NLP) Engine 122-B, Mapping Engine 122-C, Content Relevancy Engine 122-D, Update Engine 122-E, and Feedback Analyzer Engine 122-F.

Figure 2:
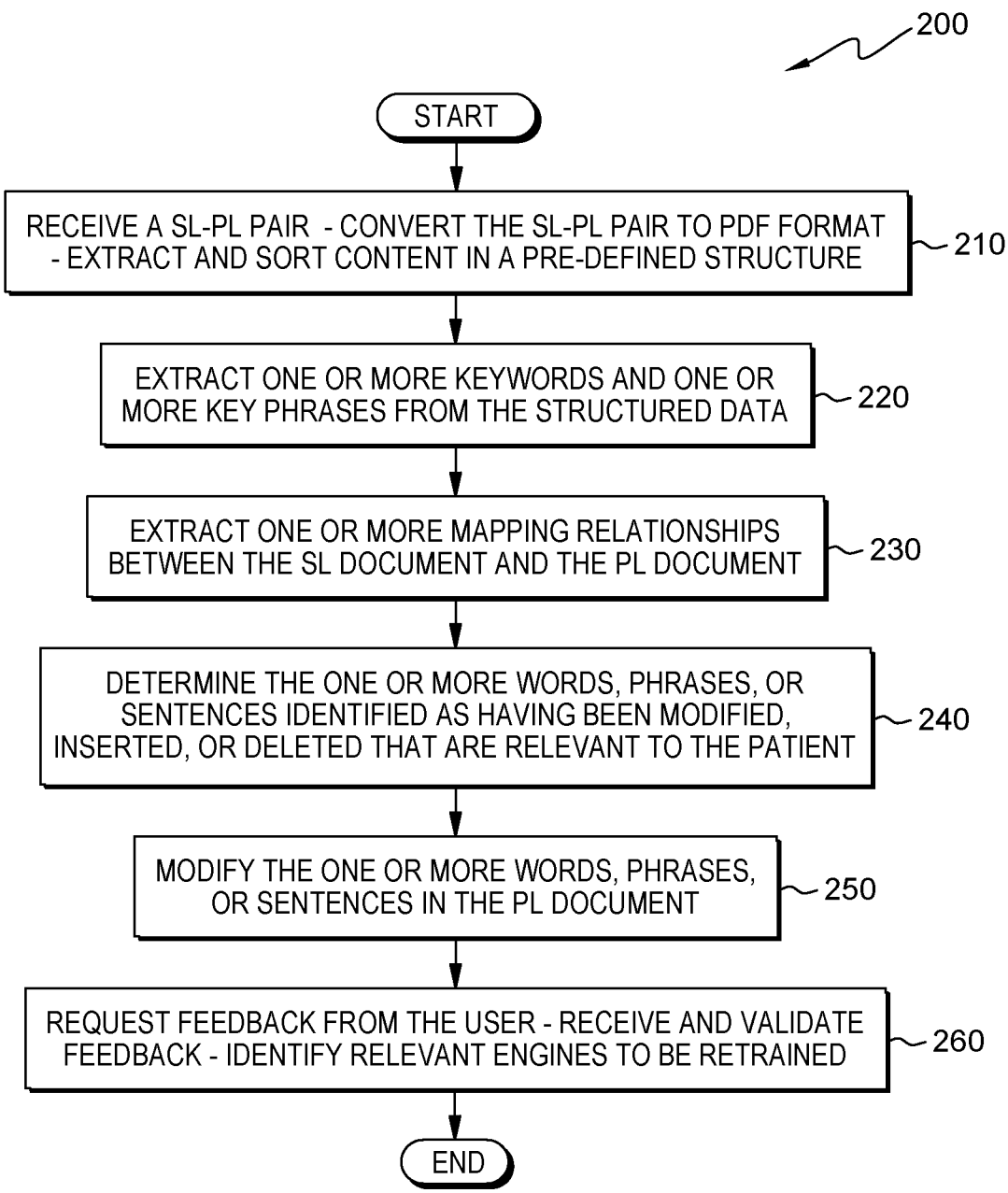
FIG. 2 is a flowchart illustrating the operational steps of an intelligent patient labeling program, on a server within the distributed data processing environment of FIG. 1, in accordance with an embodiment of the present invention.

The operational steps of intelligent patient labeling program 122 are depicted and described in further detail with respect to FIG. 2. An exemplary diagram illustrating the operational steps of intelligent patient labeling program 122 is depicted and described in further detail with respect to FIG. 3. An exemplary diagram illustrating the operational steps of PDF parser engine 122-A of intelligent patient labeling program 122 is depicted and described in further detail with respect to FIG. 4. An exemplary diagram illustrating the operational steps of NLP engine 122-B of intelligent patient labeling program 122 is depicted and described in further detail with respect to FIG. 5. An exemplary diagram illustrating the operational steps of mapping engine 122-C of intelligent patient labeling program 122 is depicted and described in further detail with respect to FIG. 6. An exemplary diagram illustrating the operational steps of content relevancy engine 122-D of intelligent patient labeling program 122 is depicted and described in further detail with respect to FIG. 7. An exemplary diagram illustrating the operational steps of update engine 122-E of intelligent patient labeling program 122 is depicted and described in further detail with respect to FIG. 8. An exemplary illustration of an analysis of an inserted key phrase by intelligent patient labeling program 122 is depicted and described in further detail with respect to FIG. 9A. An exemplary illustration of an analysis of an inserted sentence by intelligent patient labeling program 122 is depicted and described in further detail with respect to FIG. 9B. An exemplary diagram illustrating the operational steps of feedback analyzer engine 122-F of intelligent patient labeling program 122 is depicted and described in further detail with respect to FIG. 9. An exemplary flowchart illustrating the operational steps of intelligent patient labeling program 122 is depicted and described in further detail with respect to FIG. 10.

PDF Parser Engine 122-A operates to extract content from a portable document format (PDF) document of a Scientific Drug Label in a pre-defined structure and sort the structured data into a corresponding section heading and/or a corresponding section subheading.

NLP Engine 122-B operates to extract one or more keywords and/or one or more key phrases from the structured data using a custom-trained Spacey model in order to understand the concept of each sentence of the structured data.

Mapping Engine 122-C operates to extract one or more mapping relationships between the Scientific Drug Label (SL) document in JavaScript Object Notation (JSON) format and the Patient Drug Label (PL) document in JSON format in terms of their section and/or sub-section relationships or in terms of their interdependent and parent-child section/sub-section relationships using a knowledge graph.

Content Relevancy Engine 122-D operates to determine whether the one or more words, phrases, and/or sentences identified in the simplified SL document that have been modified, inserted, and/or deleted are relevant to a patient.

Update Engine 122-E operates to classify the one or more words, phrases, and/or sentences that have been modified, inserted, and/or deleted into one or more categories. When a word, phrase, or sentence is completely inserted in the original SL document, update engine 122-E searches for the correct location where the word, phrase, or sentence needs to be inserted into the original PL document based on contextual similarities of PL sentences and inserts the word, phrase, or sentence into the chosen location of the original PL document. When a word, phrase, or sentence is completely deleted from the original SL document, update engine 122-E searches for a word, phrase, or sentence in the original PL document which closely matches the word, phrase, or sentence deleted from the original SL document contextually and/or semantically and deletes the word, phrase, or sentence in the original PL document which closely matches the word, phrase, or sentence deleted from the original SL document contextually and/or semantically.

Feedback Analyzer Engine 122-F operates to receive and validate feedback from the user. Feedback Analyzer Engine 122-F also operates to identify the relevant engines to be retrained, separate the feedback, automatically annotate the feedback, and store the feedback in a database to be used later to retrain the relevant engines.

In an embodiment, the user of user computing device 130 registers with server 120. For example, the user completes a registration process (e.g., user validation), provides information to create a user profile, and authorizes the collection, analysis, and distribution (i.e., opts-in) of relevant data on identified computing devices (e.g., on user computing device 130) by server 120 (e.g., via intelligent patient labeling program 122). Relevant data includes, but is not limited to, personal information or data provided by the user or inadvertently provided by the user's device without the user's knowledge; tagged and/or recorded location information of the user (e.g., to infer context (i.e., time, place, and usage) of a location or existence); time stamped temporal information (e.g., to infer contextual reference points); and specifications pertaining to the software or hardware of the user's device. In an embodiment, the user opts-in or opts-out of certain categories of data collection. For example, the user can opt-in to provide all requested information, a subset of requested information, or no information. In one example scenario, the user opts-in to provide time-based information, but opts-out of providing location-based information (on all or a subset of computing devices associated with the user). In an embodiment, the user opts-in or opts-out of certain categories of data analysis. In an embodiment, the user opts-in or opts-out of certain categories of data distribution. Such preferences can be stored in database 124.

Database 124 operates as a repository for data received, used, and/or generated by intelligent patient labeling program 122. A database is an organized collection of data. Data includes, but is not limited to, information about user preferences (e.g., general user system settings, such as alert notifications for user computing device 130); information about alert notification preferences; a SL-PL pair; a set of trained data; feedback received from the user; and any other data received, used, and/or generated by intelligent patient labeling program 122.

Database 124 can be implemented with any type of device capable of storing data and configuration files that can be accessed and utilized by server 120, such as a hard disk drive, a database server, or a flash memory. In an embodiment, database 124 is accessed by intelligent patient labeling program 122 to store and/or to access the data. In the depicted embodiment, database 124 resides on server 120. In another embodiment, database 124 may reside on another computing device, server, cloud server, or spread across multiple devices elsewhere (not shown) within distributed data processing environment 100, provided that intelligent patient labeling program 122 has access to database 124.

The present invention may contain various accessible data sources, such as database 124, that may include personal and/or confidential company data, content, or information the user wishes not to be processed. Processing refers to any operation, automated or unautomated, or set of operations such as collecting, recording, organizing, structuring, storing, adapting, altering, retrieving, consulting, using, disclosing by transmission, dissemination, or otherwise making available, combining, restricting, erasing, or destroying personal and/or confidential company data. Intelligent patient labeling program 122 enables the authorized and secure processing of personal data.

Intelligent patient labeling program 122 provides informed consent, with notice of the collection of personal and/or confidential data, allowing the user to opt-in or opt-out of processing personal and/or confidential data. Consent can take several forms. Opt-in consent can impose on the user to take an affirmative action before personal and/or confidential data is processed. Alternatively, opt-out consent can impose on the user to take an affirmative action to prevent the processing of personal and/or confidential data before personal and/or confidential data is processed. Intelligent patient labeling program 122 provides information regarding personal and/or confidential data and the nature (e.g., type, scope, purpose, duration, etc.) of the processing. Intelligent patient labeling program 122 provides the user with copies of stored personal and/or confidential company data. Intelligent patient labeling program 122 allows the correction or completion of incorrect or incomplete personal and/or confidential data. Intelligent patient labeling program 122 allows for the immediate deletion of personal and/or confidential data.

User computing device 130 operates to run user interface 132 through which a user can interact with intelligent patient labeling program 122 on server 120. In an embodiment, user computing device 130 is a device that performs programmable instructions. For example, user computing device 130 may be an electronic device, such as a laptop computer, a tablet computer, a netbook computer, a personal computer, a desktop computer, a smart phone, or any programmable electronic device capable of running user interface 132 and of communicating (i.e., sending and receiving data) with intelligent patient labeling program 122 via network 110. In general, user computing device 130 represents any programmable electronic device or a combination of programmable electronic devices capable of executing machine readable program instructions and communicating with other computing devices (not shown) within distributed data processing environment 100 via network 110. In the depicted embodiment, user computing device 130 includes an instance of user interface 132.

User interface 132 operates as a local user interface between intelligent patient labeling program 122 on server 120 and a user of user computing device 130. In some embodiments, user interface 132 is a graphical user interface (GUI), a web user interface (WUI), and/or a voice user interface (VUI) that can display (i.e., visually) or present (i.e., audibly) text, documents, web browser windows, user options, application interfaces, and instructions for operations sent from intelligent patient labeling program 122 to a user via network 110. User interface 132 can also display or present alerts including information (such as graphics, text, and/or sound) sent from intelligent patient labeling program 122 to a user via network 110. In an embodiment, user interface 132 is capable of sending and receiving data (i.e., to and from intelligent patient labeling program 122 via network 110, respectively). Through user interface 132, a user can opt-in to intelligent patient labeling program 122; create a user profile; set user preferences and alert notification preferences; receive an alert notification; input a Scientific Drug Label-Patient Drug Label pair; receive the updated Patient Drug Label; receive a request for feedback; and input feedback.

A user preference is a setting that can be customized for a particular user. A set of default user preferences are assigned to each user of intelligent patient labeling program 122. A user preference editor can be used to update values to change the default user preferences. User preferences that can be customized include, but are not limited to, general user system settings, specific user profile settings, alert notification settings, and machine-learned data collection/storage settings. Machine-learned data is a user's personalized corpus of data. Machine-learned data includes, but is not limited to, past results of iterations of intelligent patient labeling program 122.

FIG. 2 is a flowchart, generally designated 200, illustrating the operational steps of intelligent patient labeling program 122, on server 120 within distributed data processing environment 100 of FIG. 1, in accordance with an embodiment of the present invention. In an embodiment, intelligent patient labeling program 122 operates to automatically identify one or more updates in a Scientific Drug Label relevant to a patient; to identify the type of update and the appropriate position of the update in a Patient Drug Label; to transform the complex medical language of the update into simple patient learning language without losing contextual information; and to incorporate the update into the Patient Drug Label. It should be appreciated that the process depicted in FIG. 2 illustrates one possible iteration of the process flow, which may be repeated each time a Scientific Drug Label (SL)-Patient Drug Label (PL) pair is received. In another embodiment, the process depicted in FIG. 2 may be repeated each time intelligent patient labeling program 122 detects an update in a Scientific Drug Label-Patient Drug Label pair.

In step 210, intelligent patient labeling program 122 (hereinafter referred to as "program 122") receives a Scientific Drug Label (SL)-Patient Drug Label (PL) pair. In an embodiment, program 122 receives a SL-PL pair as an input from a user through a user computing device (e.g., user computing device 130) via a user interface (e.g., user interface 132). The user may be, but is not limited to, a pharmaceutical company representative or a medical device company representative. The SL-PL pair is a set of documents representing a pharmaceutical drug or medical device (hereinafter "pharmaceutical drug" means either a pharmaceutical drug or a medical device). The SL-PL pair is inputted when a pharmaceutical drug is released to the market and/or when a pharmaceutical drug currently on the market is changed in some way (i.e., one or more keywords and/or one or more key phrases in the Scientific Drug Label of the SL-PL pair have been modified, inserted, and/or deleted, but the Patient Drug Label of the SL-PL pair has not been updated). In another embodiment, program 122 monitors a database (e.g., database 124) for one or more recent updates to SL-PL pairs stored in the database (e.g., database 124).

In an embodiment, program 122 converts the Scientific Drug Label and the Patient Drug Label of the SL-PL pair from a word format to a PDF using a digitization module. The digitization module is a word-to-PDF convertor that converts a document in word format to a document in PDF format, tracks the changes made to the document, and accepts and/or rejects the tracked changes). In an embodiment, program 122 sends the PDF document of the Scientific Drug Label and the Patient Drug Label of the SL-PL pair (i.e., a SL .pdf and a PL .pdf) to PDF parser 122-A of program 122.

In an embodiment, PDF parser engine 122-A of program 122 extracts content from the Scientific Drug Label in a pre-defined structure (hereinafter referred to as the "structured data"). The pre-defined structure may be, but is not limited to, an Extensible Markup Language (XML) format. In an embodiment, PDF parser engine 122-A of program 122 processes the extracted content from the document using an XML parsing module. The XML parsing module has two inner modules: a first module to extract a section heading and/or a subsection heading and a second module to extract data.

In an embodiment, PDF parser engine 122-A of program 122 sorts the structured data. In an embodiment, PDF parser engine 122-A of program 122 sorts the structured data into a corresponding section heading and/or a corresponding section subheading. In an embodiment, PDF parser engine 122-A of program 122 sorts the structured data in a structured JSON format using a JSON formatter module. In an embodiment, PDF parser engine 122-A of program 122 sends the structured data to NLP engine 122-B of program 122.

In step 220, NLP engine 122-B of program 122 extracts one or more keywords and/or one or more key phrases from the structured data. In an embodiment, NLP engine 122-B of program 122 extracts one or more keywords and/or one or more key phrases from the structured data using a custom-trained Spacey model. In an embodiment, NLP engine 122-B of program 122 extracts one or more keywords and/or one or more key phrases in order to understand the concept of each sentence of the structured data. The one or more keywords and/or the one or more key phrases extracted from the structured data may include, but are not limited to, a name of a drug (i.e., associated with the SL-PL pair), a composition of the drug, a shape and/or appearance of the drug, a medical condition treated by the drug, a method to administer the drug, one or more side effects a patient may experience when taking the drug (i.e., one or more unwanted or unexpected symptoms or feelings that may occur when taking the drug), and one or more precautions a patient should take when using the drug.

In an embodiment, program 122 trains NLP engine 122-B of program 122 to generate a model for the one or more keywords and/or the one or more key phrases extracted. In an embodiment, program 122 determines a position of the one or more keywords and/or the one or more key phrases extracted. In an embodiment, program 122 determines a category of the one or more keywords and/or the one or more key phrases extracted. In an embodiment, program 122 creates an annotation for the position and/or the category of the one or more keywords and/or the one or more key phrases. In an embodiment, program 122 trains NLP engine 122-B of program 122 on the annotation created for the position and/or the category of the one or more keywords and/or the one or more key phrases using a deep learning algorithm. In an embodiment, program 122 tests and validates the trained data. In an embodiment, program 122 stores the trained data in a dictionary in the database (e.g., database 124).

In an embodiment, NLP engine 122-B of program 122 sends the documents in JSON format (i.e., a SL document in JSON format and a PL document in JSON format) to mapping engine 122-C of program 122. In an embodiment, NLP engine 122-B of program 122 sends mapping configuration files obtained from a Quality Review of Documents (QRD) template to mapping engine 122-C of program 122.

In step 230, mapping engine 122-C of program 122 extracts one or more mapping relationships between the SL document in JSON format and the PL document in JSON format. In an embodiment, mapping engine 122-C of program 122 extracts one or more mapping relationships between the SL document in JSON format and the PL document in JSON format in terms of their section and/or sub-section relationships using a knowledge graph. In an embodiment, mapping engine 122-C of program 122 extracts one or more mapping relationships between the SL document in JSON format and the PL document in JSON format in terms of their interdependent and parent-child section/sub-section relationships using a knowledge graph.

The one or more mapping relationships between the SL document in JSON format and the PL document in JSON format may include, but is not limited to, SL-PL direct section/sub-section, SL-SL interdependent section/sub-section, SL-SL parent-child, and PL-PL parent-child. In an embodiment, mapping engine 122-C of program 122 extracts a confidence score for each mapping relationship between the SL document in JSON format and the PL document in JSON format based on contextual information.

In an embodiment, mapping engine 122-C of program 122 sends the extracted mapping relationships between the SL document in JSON format and the PL document in JSON format to update engine 122-E of program 122 (i.e., as a mapping document in JSON format). In an embodiment, mapping engine 122-C of program 122 sends the SL document in JSON format and the PL document in JSON format to content relevancy engine 122-D of program 122.

In step 240, in a training stage, content relevancy engine 122-D of program 122 converts the original SL document into a simplified patient friendly language using a transformation module. In an embodiment, content relevancy engine 122-D of program 122 analyzes the simplified SL document to identify the one or more words, phrases, and/or sentences that have been modified, inserted, and/or deleted. In an embodiment, content relevancy engine 122-D of program 122 determines whether the one or more words, phrases, and/or sentences identified are relevant to a patient. In an embodiment, content relevancy engine 122-D of program 122 labels as "relevant" the one or more words, phrases, and/or sentences determined to be relevant to the patient. In an embodiment, content relevancy engine 122-D of program 122 labels as "irrelevant" the one or more words, phrases, and/or sentences determined to be irrelevant to the patient. In an embodiment, content relevancy engine 122-D of program 122 determines the label given to the one or more words, phrases, and/or sentences using a smart system. In an embodiment, content relevancy engine 122-D of program 122 enables the smart system to perform unsupervised learning. The labels are not specified. The smart system determines the label based on an intelligent comparison model. The intelligent comparison model is a bidirectional transformer. In an embodiment, content relevancy engine 122-D of program 122 trains the smart decision-making context similarity model for future cases using the labeled data.

In another embodiment, in an inference stage, content relevancy engine 122-D of program 122 converts the original SL document into a simplified patient friendly language using a transformation module. In an embodiment, content relevancy engine 122-D of program 122 sends the simplified SL document to a smart decision-making context similarity module to determine whether the one or more words, phrases, and/or sentences identified are relevant to a patient. The decision-making context similarity module has human-like decision making capabilities. For example, certain information such as drug interactions are relevant to a practitioner, but not to a patient. Therefore, content relevancy engine 122-D of program 122 determines the new sentence in the SL document is not relevant to the patient and, therefore, will be omitted from the PL document.

In an embodiment, content relevancy engine 122-D of program 122 sends the original SL document and the simplified SL document to update engine 122-E of program 122. The extracted mapping relationships between the original SL document and the original PL document (i.e., the mapping documents in JSON format) were previously sent to update engine 122-E of program 122 in step 230.

In step 250, update engine 122-E of program 122 classifies the one or more words, phrases, and/or sentences that have been modified, inserted, and/or deleted into one or more categories. There are three (3) categories that include: complete insertion of a sentence in the original SL document, complete deletion of a sentence in the original SL document, and insertion and/or deletion of words and/or phrases in a sentence in the original SL document.

In an embodiment, if a sentence is completely inserted in the original SL document, update engine 122-E of program 122 classifies the sentence into one or more relevant categories. In an embodiment, update engine 122-E of program 122 searches for the correct location where the sentence needs to be inserted into the original PL document based on contextual similarities of PL sentences. In an embodiment, update engine 122-E of program 122 inserts the sentence into the chosen location of the original PL document.

In an embodiment, if a sentence is completely deleted from the original SL document, update engine 122-E of program 122 classifies the sentence into one or more relevant categories. In an embodiment, update engine 122-E of program 122 searches for a sentence in the original PL document which closely matches the sentence deleted from the original SL document contextually and/or semantically. In an embodiment, update engine 122-E of program 122 deletes the sentence in the original PL document that closely matches the sentence deleted from the original SL document contextually and/or semantically.

In an embodiment, if a word is inserted in the original SL document, update engine 122-E of program 122 classifies the word into one or more relevant categories. In an embodiment, update engine 122-E of program 122 searches for a sentence that closely maps to the word inserted on a sentence level. In an embodiment, update engine 122-E of program 122 searches for the correct location where the word needs to be inserted into the original PL document based on contextual similarities. In an embodiment, update engine 122-E of program 122 inserts the word into the chosen location of the original PL document.

In an embodiment, if a word is deleted from the original SL document, update engine 122-E of program 122 classifies the word into one or more relevant categories. In an embodiment, update engine 122-E of program 122 searches for a sentence in the original PL document that closely matches the word deleted from the original SL document contextually and/or semantically. In an embodiment, update engine 122-E of program 122 deletes the word in the sentence in the original PL document that closely matches the word deleted from the original SL document contextually and/or semantically.

In step 260, feedback analyzer engine 122-F of program 122 requests feedback from the user. In an embodiment, feedback analyzer engine 122-F of program 122 requests feedback from the user through the user computing device (e.g., user computing device 130) via the user interface (user interface 132). In an embodiment, feedback analyzer engine 122-F of program 122 enables the user to input feedback through the user computing device (e.g., user computing device 130) via the user interface (user interface 132). The feedback input by the user may include, but is not limited to, a verification or rejection of the PL documents outputted and an acceptance or rejection of the updates, insertions, and/or deletions. In an embodiment, feedback analyzer engine 122-F of program 122 receives feedback from the user. In an embodiment, feedback analyzer engine 122-F of program 122 validates the feedback received from the user manually using the confidence scores of intermediate outputs (i.e., of each individual engine). In an embodiment, feedback analyzer engine 122-F of program 122 identifies the relevant engines to be retrained. In an embodiment, feedback analyzer engine 122-F of program 122 separates the feedback received from the user (e.g., based on the model that will be used to retrain the relevant engines). In an embodiment, feedback analyzer engine 122-F of program 122 automatically annotates the feedback received from the user. In an embodiment, feedback analyzer engine 122-F of program 122 stores the feedback received from the user in a database (e.g., database 124) to be used later to retrain the relevant engines.

Figure 3:
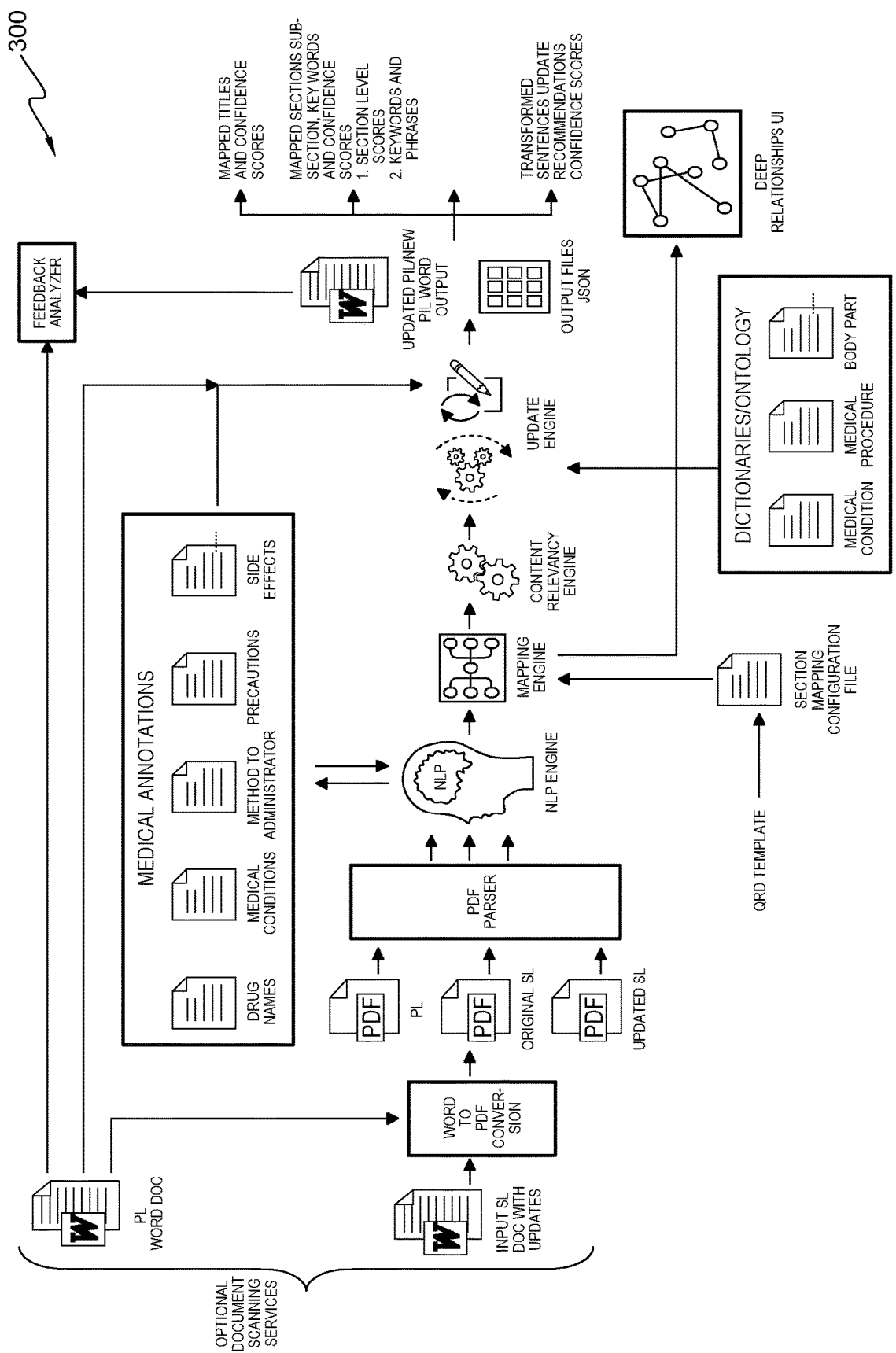
FIG. 3 is an exemplary diagram illustrating the operational steps of the intelligent patient labeling program, on the server within the distributed data processing environment of FIG. 1, in accordance with an embodiment of the present invention.

FIG. 3 is an exemplary diagram, generally designated 300, illustrating the operational steps of program 122, on server 120 within distributed data processing environment 100 of FIG. 1, in accordance with an embodiment of the present invention. The operational steps of program 122 are the same as described in FIG. 2.

Figure 4:
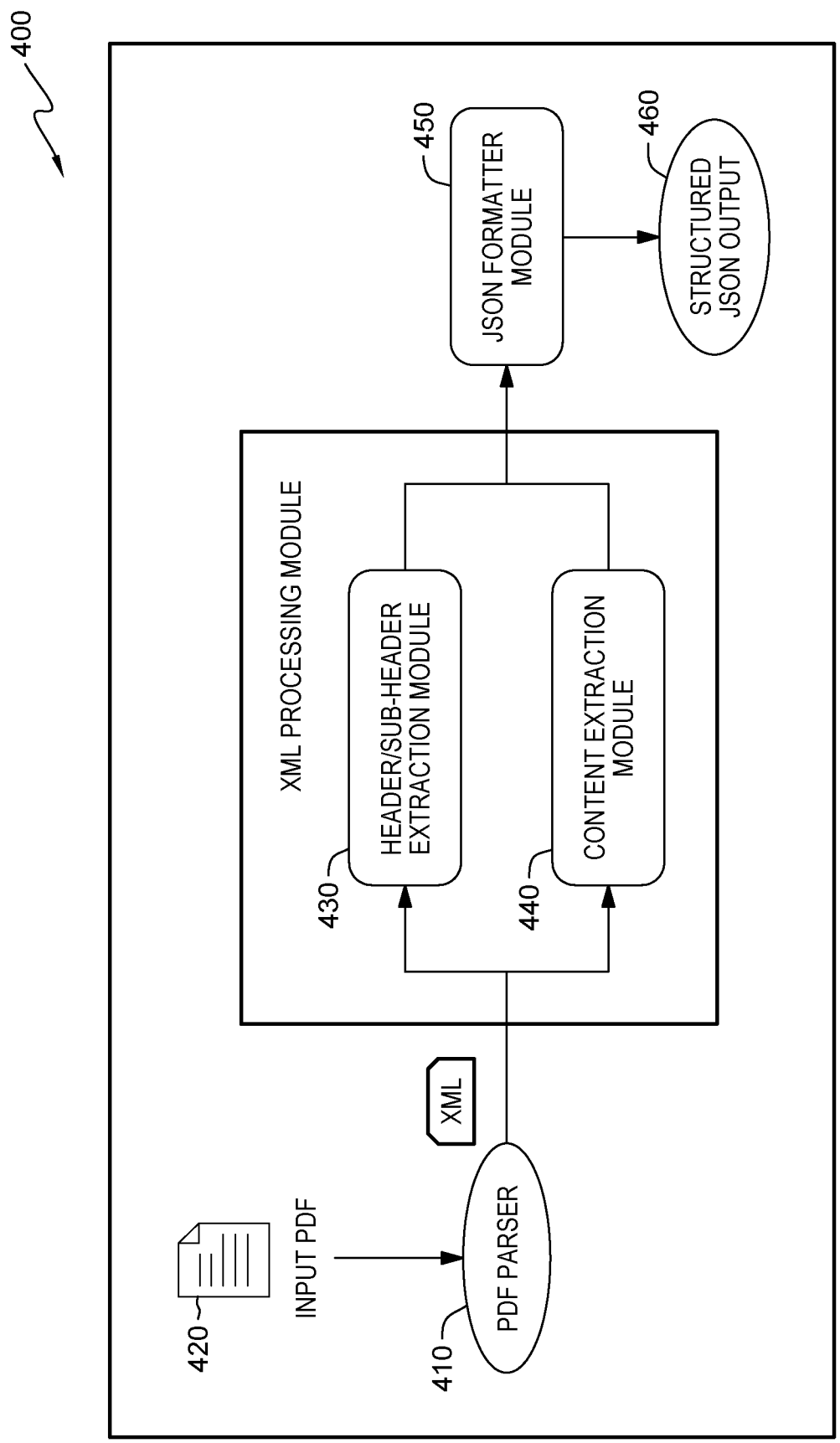
FIG. 4 is an exemplary diagram illustrating the operational steps of a PDF parser engine of the intelligent patient labeling program, on the server within the distributed data processing environment of FIG. 1, in accordance with an embodiment of the present invention.

FIG. 4 is an exemplary diagram, generally designated 400, illustrating the operational steps of PDF parser engine 122-A of program 122, on server 120 within distributed data processing environment 100 of FIG. 1, in accordance with an embodiment of the present invention. PDF parser 122-A (e.g., 410) receives an input. The input is a PDF document (e.g., 420) of the Scientific Drug Label and the Patient Drug Label of the SL-PL pair (i.e., a SL .pdf and a PL .pdf). PDF parser 122-A extracts content from the Scientific Drug Label in an XML format. PDF parser engine 122-A processes the extracted content using an XML processing module. The XML processing module has two inner modules: a first module (e.g., 430) to extract a section heading and/or a subsection heading and a second module (e.g., 440) to extract data. PDF parser engine 122-A sorts the structured data into a corresponding section heading and/or a corresponding section subheading in a structured j son format using a j son formatter module (e.g., 450). PDF parser engine 122-A sends the structured data (e.g., 460) to NLP engine 122-B.

Figure 5:
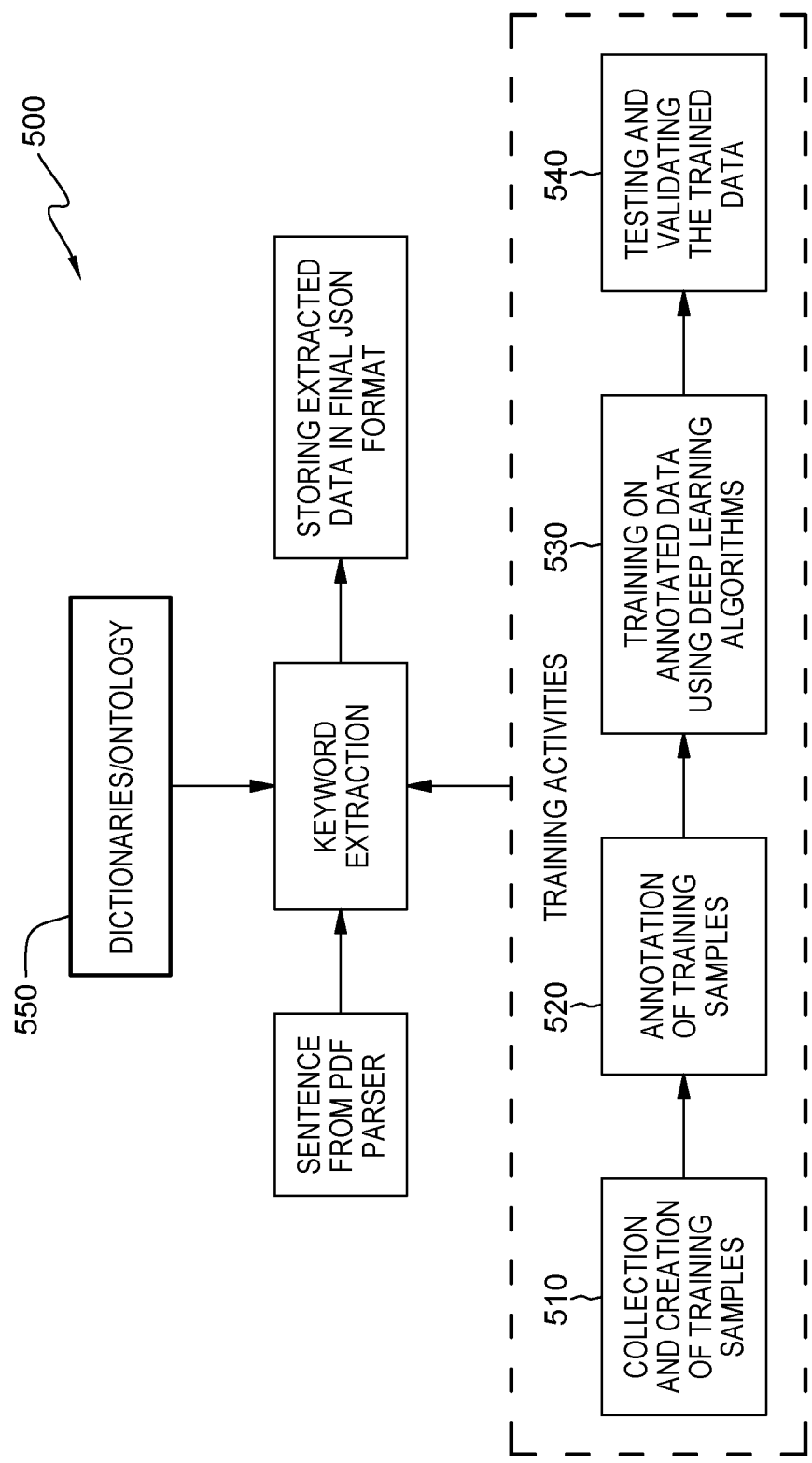
FIG. 5 is an exemplary diagram illustrating the operational steps of a natural language processing engine of the intelligent patient labeling program, on the server within the distributed data processing environment of FIG. 1, in accordance with an embodiment of the present invention.

FIG. 5 is an exemplary diagram, generally designated 500, illustrating the operational steps of NLP engine 122-B of program 122, on server 120 within the distributed data processing environment 100 of FIG. 1, in accordance with an embodiment of the present invention. NLP engine 122-B extracts one or more keywords and/or one or more key phrases (e.g., 510) from the structured data using a custom-trained Spacey model in order to understand the concept of each sentence of the structured data. Program 122 trains NLP engine 122-B to generate a model for the one or more keywords and/or the one or more key phrases extracted. Program 122 determines a position and/or a category of the one or more keywords and/or the one or more key phrases extracted (e.g., 510). Program 122 creates an annotation for the position and/or the category of the one or more keywords and/or the one or more key phrases extracted (e.g., 520). Program 122 trains NLP engine 122-B on the annotation created for the position and/or the category of the one or more keywords and/or the one or more key phrases using a deep learning algorithm (e.g., 530). Program 122 tests and validates the trained data (e.g., 540). Program 122 stores the trained data in a dictionary (e.g., 550) in the database (e.g., database 124).

Figure 6:
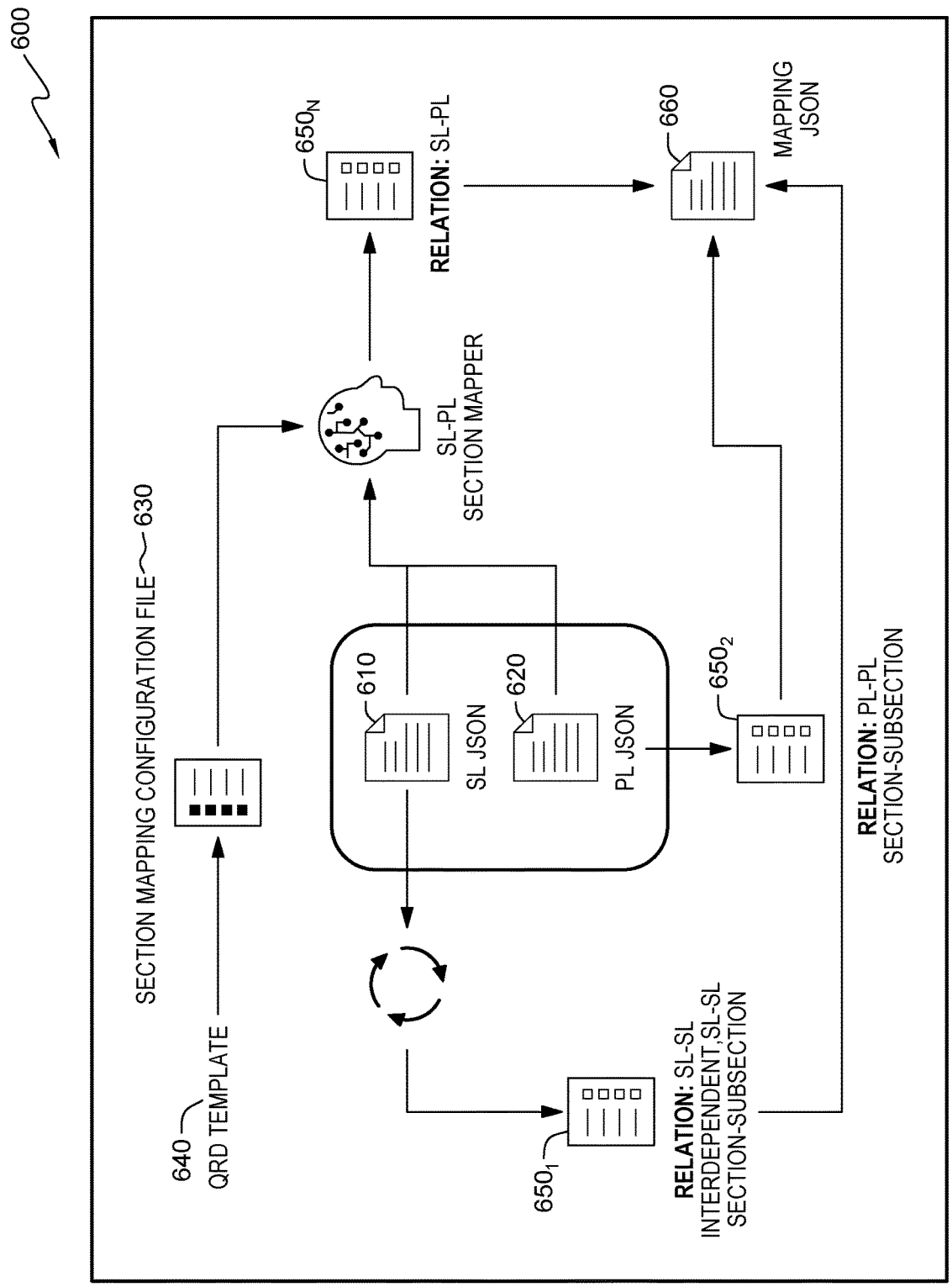
FIG. 6 is an exemplary diagram illustrating the operational steps of a mapping engine of the intelligent patient labeling program, on the server within the distributed data processing environment of FIG. 1, in accordance with an embodiment of the present invention.

FIG. 6 is an exemplary diagram, generally designated 600, illustrating the operational steps of mapping engine 122-C of program 122, on server 120 within distributed data processing environment 100 of FIG. 1, in accordance with an embodiment of the present invention. Mapping engine 122-C receives a SL document in JSON format (e.g., 610), a PL document in JSON format (e.g., 620), and mapping configuration files (e.g., 630) obtained from a QRD template (e.g., 640). Mapping engine 122-C extracts one or more mapping relationships (e.g., $650_{1-N}$) between the SL document in JSON format and the PL document in JSON format in terms of their section and/or sub-section relationships using a knowledge graph. Mapping engine 122-C extracts one or more mapping relationships between the SL document in JSON format and the PL document in JSON format in terms of their interdependent and parent-child section/sub-section relationships using a knowledge graph. The one or more mapping relationships between the SL document in JSON format and the PL document in JSON format may include, but is not limited to, SL-PL direct section/sub-section (e.g., $650_N$), SL-SL interdependent section/sub-section (e.g., $650_1$), SL-SL parent-child (e.g., $650_1$), and PL-PL parent-child (e.g., $650_2$). Mapping engine 122-C extracts a confidence score for each mapping relationship between the SL document in JSON format and the PL document in JSON format based on contextual information. Mapping engine 122-C sends the extracted mapping relationships between the SL document in JSON format and the PL document in JSON format to update engine 122-E (i.e., as a mapping document in JSON format, e.g., 660). Mapping engine 122-C sends the SL document in JSON format and the PL document in JSON format to content relevancy engine 122-D.

Figure 7:
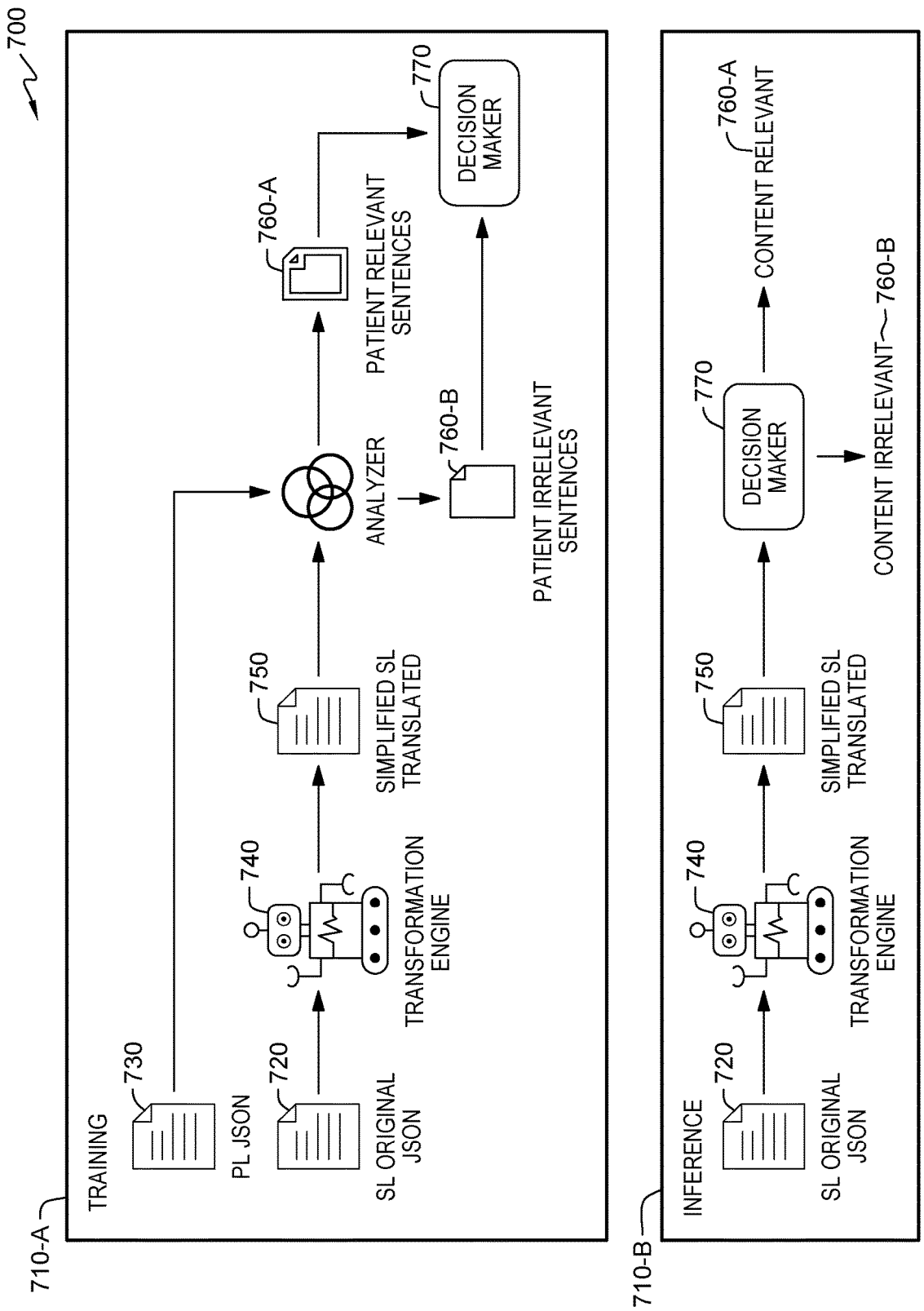
FIG. 7 is an exemplary diagram illustrating the operational steps of a content relevancy engine of the intelligent patient labeling program, on the server within the distributed data processing environment of FIG. 1, in accordance with an embodiment of the present invention.

FIG. 7 is an exemplary diagram, generally designated 700, illustrating the operational steps of content relevancy engine 122-D of program 122, on server 120 within distributed data processing environment 100 of FIG. 1, in accordance with an embodiment of the present invention. Content relevancy engine 122-D receives the original SL document in JSON format (e.g., 720) and the PL document in JSON format (e.g., 730).

In a training stage (e.g., 710-A), content relevancy engine 122-D converts the original SL document (e.g., 720) into a simplified patient friendly language using a transformation module (e.g., 740). Content relevancy engine 122-D analyzes the simplified SL document (e.g., 750) to identify the one or more words, phrases, and/or sentences that have been modified, inserted, and/or deleted. Content relevancy engine 122-D determines whether the one or more words, phrases, and/or sentences identified are relevant to a patient. Content relevancy engine 122-D of program 122 labels as "relevant" the one or more words, phrases, and/or sentences determined to be relevant to the patient. Content relevancy engine 122-D of program 122 labels as "irrelevant" the one or more words, phrases, and/or sentences determined to be irrelevant to the patient. For example, 760-A represents the one or more words, phrases, and/or sentences labeled as relevant and 760-B represents the one or more words, phrases, and/or sentences labeled as irrelevant. Content relevancy engine 122-D of program 122 determines the label given to the one or more words, phrases, and/or sentences using a smart system. Content relevancy engine 122-D of program 122 enables the smart system to perform unsupervised learning. The labels are not specified. The smart system determines the label based on an intelligent comparison model. The intelligent comparison model is a bidirectional transformer. Content relevancy engine 122-D of program 122 trains the smart decision-making context similarity model (e.g., 770) for future cases using the labeled data.

In an inference stage (e.g., 710-B), content relevancy engine 122-D converts the original SL document (e.g., 720) into a simplified patient friendly language using a transformation module (e.g., 740). Content relevancy engine 122-D sends the simplified SL document (e.g., 750) to a smart decision-making context similarity module (e.g., 770) to determine whether the one or more words, phrases, and/or sentences identified are relevant to a patient. For example, 760-A represents the one or more words, phrases, and/or sentences labeled as relevant and 760-B represents the one or more words, phrases, and/or sentences labeled as irrelevant.

Figure 8:
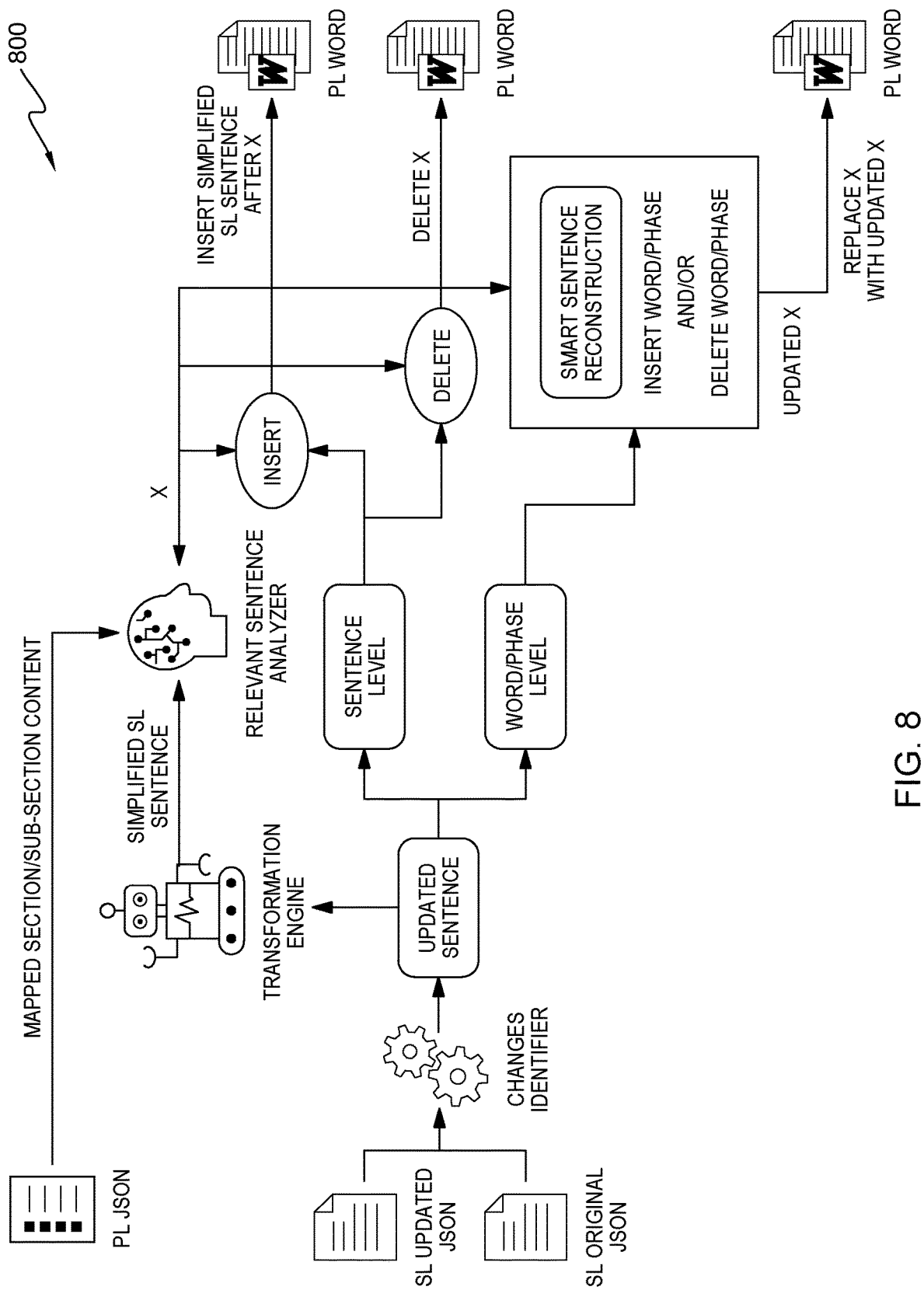
FIG. 8 is an exemplary diagram illustrating the operational steps of an update engine of the intelligent patient labeling program, on the server within the distributed data processing environment of FIG. 1, in accordance with an embodiment of the present invention.

FIG. 8 is an exemplary diagram, generally designated 800, illustrating the operational steps of update engine 122-E of program 122, on server 120 within distributed data processing environment 100 of FIG. 1, in accordance with an embodiment of the present invention. Update engine 122-E receives the original SL document, the simplified SL document, and the mapping documents in json format. Update engine 122-E classifies the one or more words, phrases, and/or sentences that have been modified, inserted, and/or deleted into one or more categories—complete insertion of a sentence in the original SL document, complete deletion of a sentence in the original SL document, and insertion and/or deletion of words and/or phrases in a sentence in the original SL document. Based on the classification of the one or more words, phrases, and/or sentences, the original PL document is updated.

If a sentence is completely inserted in the original SL document, update engine 122-E classifies the sentence into one or more relevant categories. Update engine 122-E searches for the correct location where the sentence needs to be inserted into the original PL document based on contextual similarities of PL sentences. Update engine 122-E inserts the sentence into the chosen location of the original PL document.

If a sentence is completely deleted from the original SL document, update engine 122-E classifies the sentence into one or more relevant categories. Update engine 122-E searches for a sentence in the original PL document that closely matches the sentence deleted from the original SL document contextually and/or semantically. Update engine 122-E deletes the sentence in the original PL document which closely matches the sentence deleted from the original SL document contextually and/or semantically.

If a word is inserted in the original SL document, update engine 122-E classifies the word into one or more relevant categories. Update engine 122-E searches for a sentence that closely maps to the word inserted on a sentence level. Update engine 122-E searches for the correct location where the word needs to be inserted into the original PL document based on contextual similarities. Update engine 122-E inserts the word into the chosen location of the original PL document.

If a word is deleted from the original SL document, update engine 122-E classifies the word into one or more relevant categories. Update engine 122-E searches for a sentence in the original PL document that closely matches the word deleted from the original SL document contextually and/or semantically. Update engine 122-E deletes the word in the sentence in the original PL document which closely matches the word deleted from the original SL document contextually and/or semantically.

Figure 9B:
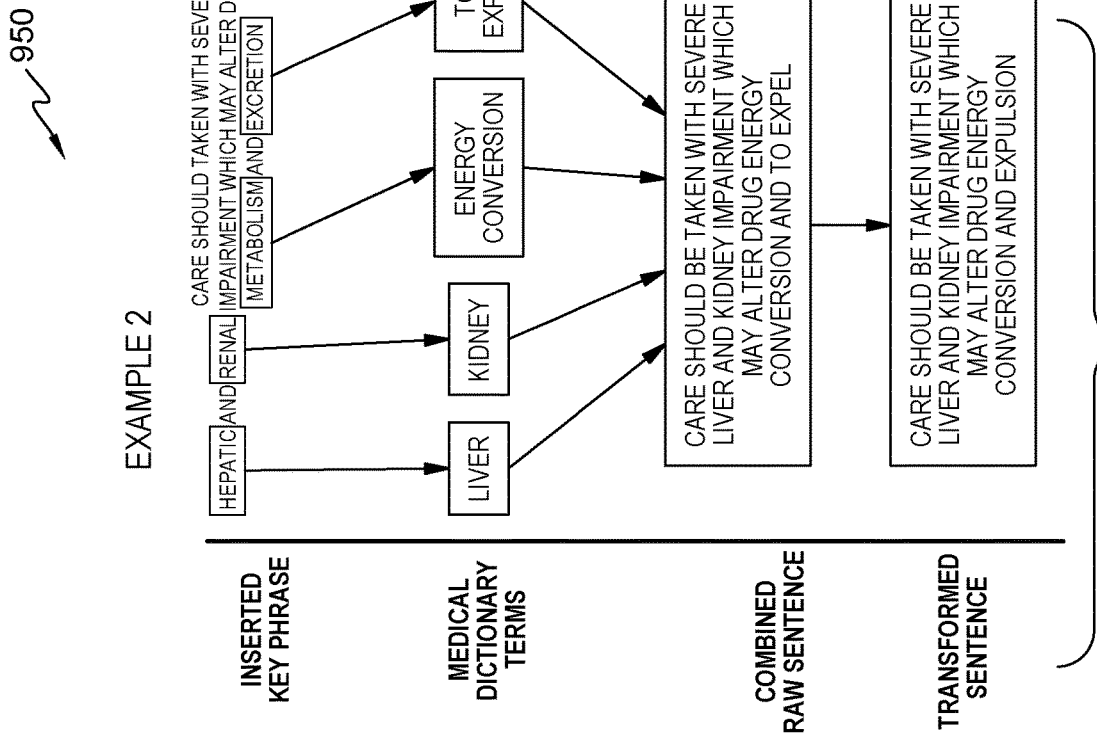
FIG. 9B is an exemplary illustration of an analysis of an inserted sentence by the intelligent patient labeling program, on the server within the distributed data processing environment of FIG. 1, in accordance with an embodiment of the present invention.
Figure 9A:
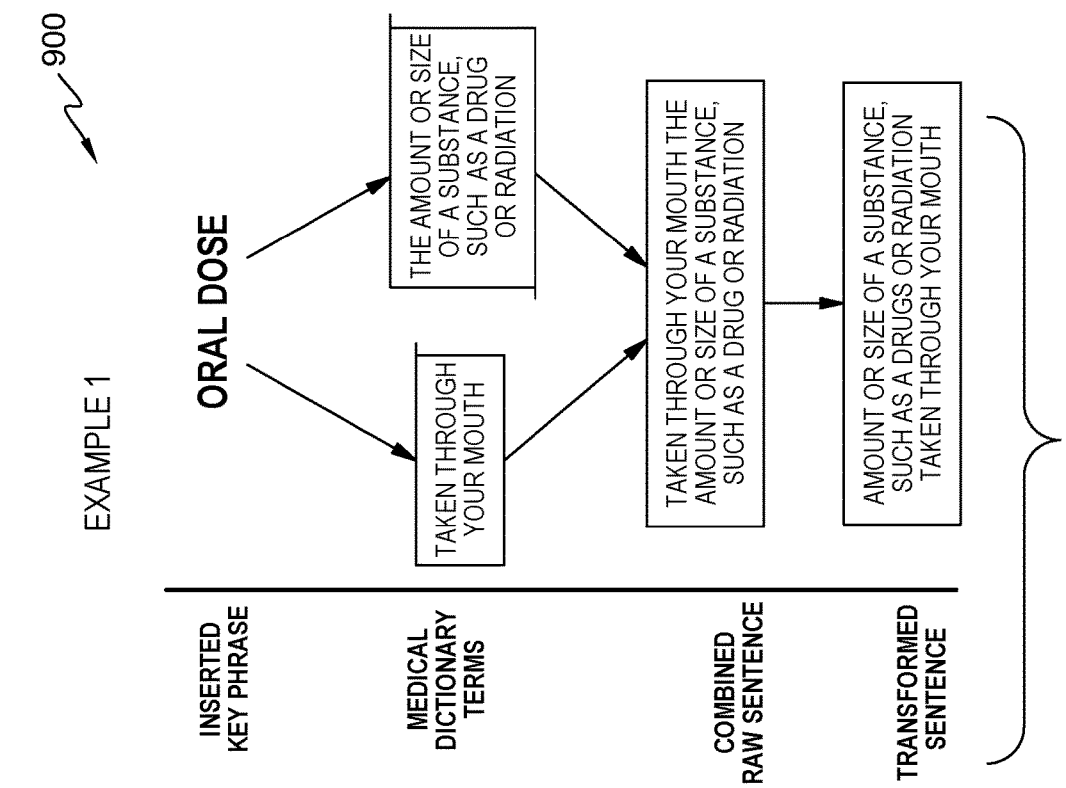
FIG. 9A is an exemplary illustration of an analysis of an inserted key phrase by the intelligent patient labeling program, on the server within the distributed data processing environment of FIG. 1, in accordance with an embodiment of the present invention.

FIG. 9A is an exemplary illustration, generally designated 900, of an analysis of an inserted key phrase by program 122, on server 120 within distributed data processing environment 100 of FIG. 1, in accordance with an embodiment of the present invention.

FIG. 9B is an exemplary illustration, generally designated 950, of an analysis of an inserted sentence by program 122, on server 120 within distributed data processing environment 100 of FIG. 1, in accordance with an embodiment of the present invention.

Figure 10:
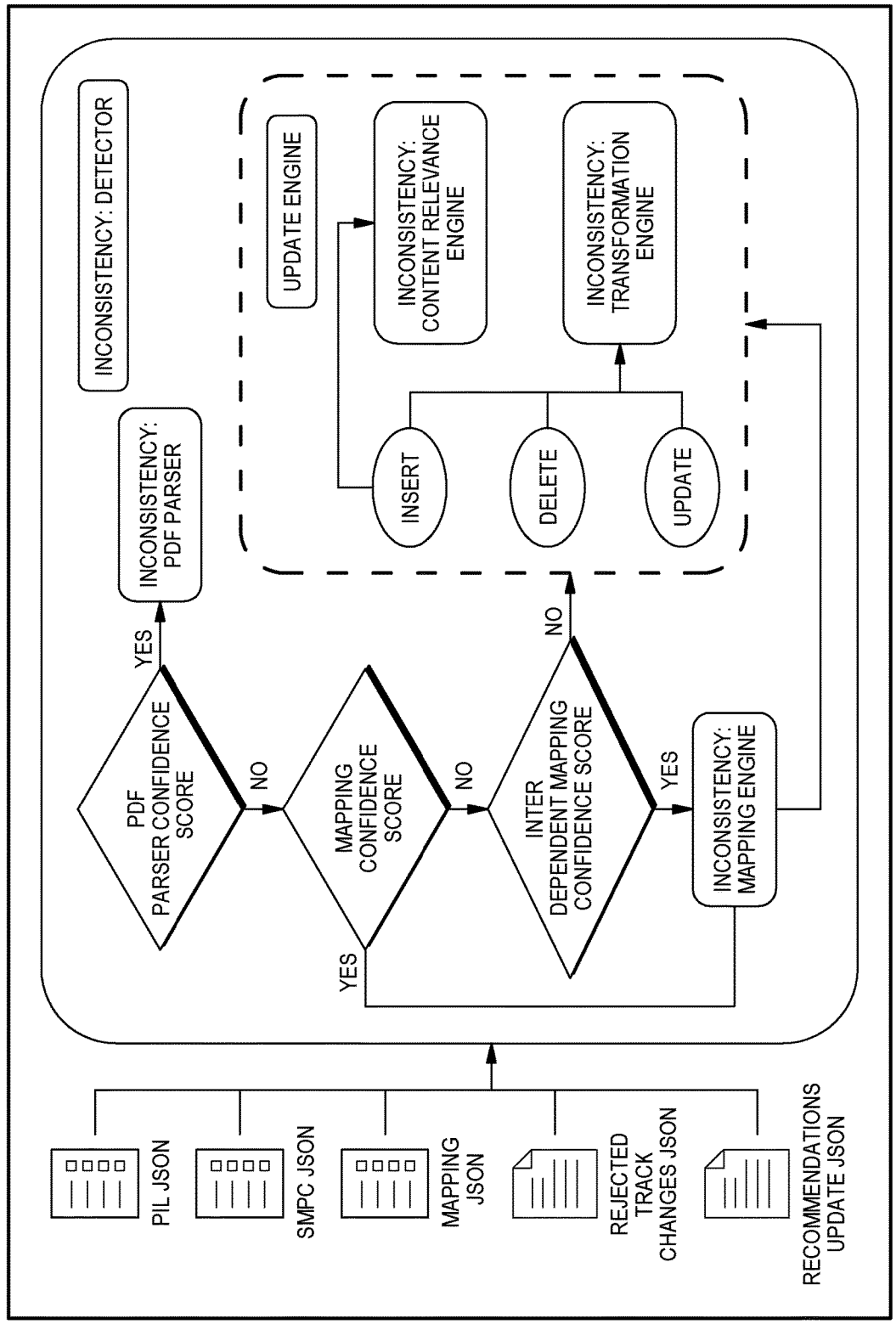
FIG. 10 is an exemplary flowchart illustrating the operational steps of the intelligent patient labeling program, on the server within the distributed data processing environment of FIG. 1, in accordance with an embodiment of the present invention.

FIG. 10 is an exemplary flowchart, generally designated 1000, illustrating the operational steps of program 122, on server 120 within distributed data processing environment 100 of FIG. 1, in accordance with an embodiment of the present invention. The operational steps of program 122 are the same as described in FIG. 2.

Figure 11:
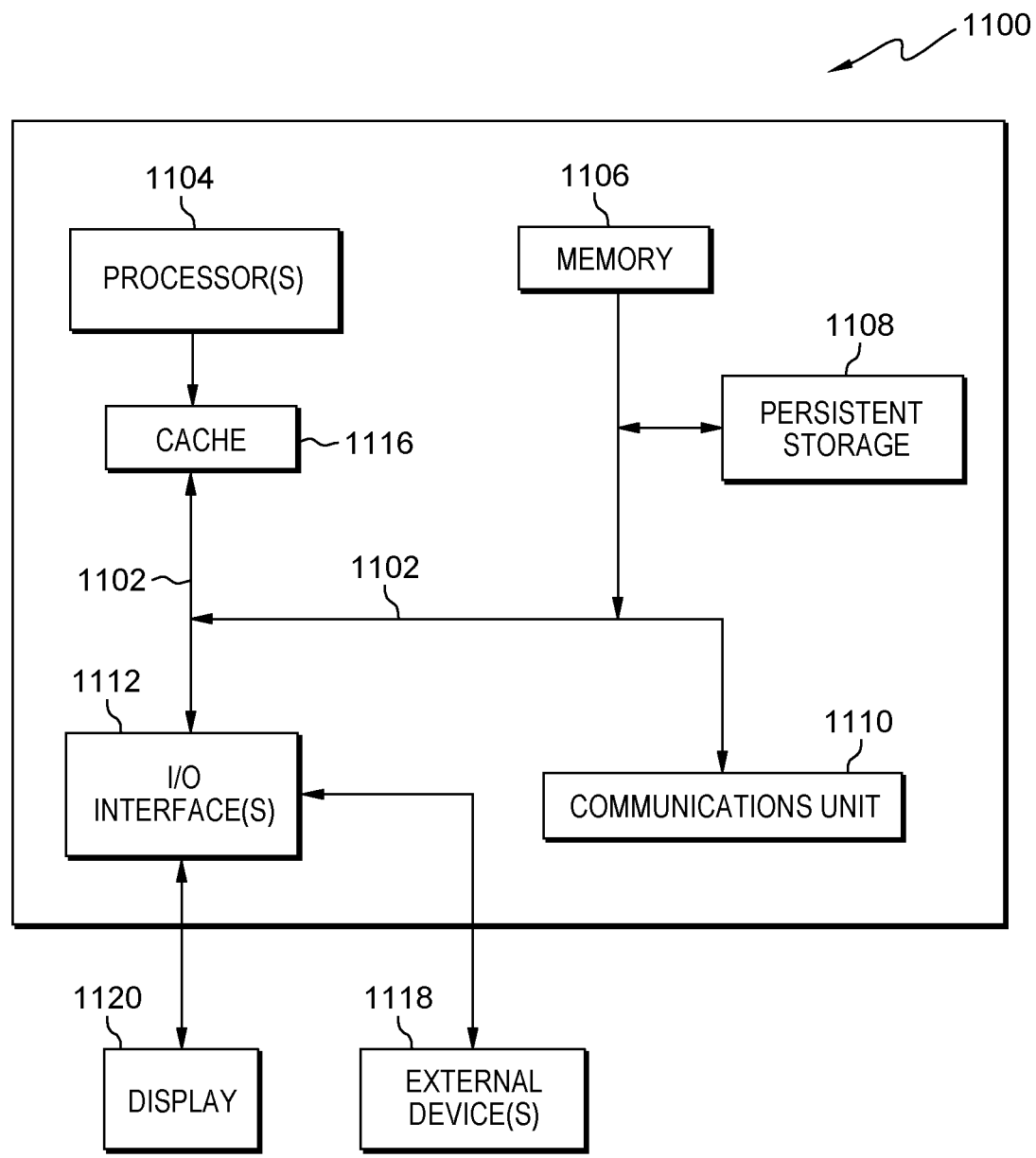
FIG. 11 is a block diagram illustrating the components of the server within the distributed data processing environment of FIG. 1, in accordance with an embodiment of the present invention.

FIG. 11 is a block diagram illustrating the components of computing device 1100 (e.g., server 120) within distributed data processing environment 100 of FIG. 1, in accordance with an embodiment of the present invention. It should be appreciated that FIG. 11 provides only an illustration of one implementation and does not imply any limitations with regard to the environments in which different embodiments can be implemented. Many modifications to the depicted environment can be made. Computing device 1100 includes processor(s) 1104, memory 1106, cache 1116, communications fabric 1102, persistent storage 1108, input/output (I/O) interface(s) 1112, and communications unit 1110. Communications fabric 1102 provides communications between memory 1106, cache 1116, persistent storage 1108, input/output (I/O) interface(s) 1112, and communications unit 1110. Communications fabric 1102 can be implemented with any architecture designed for passing data and/or control information between processors (such as microprocessors, communications and network processors, etc.), system memory, peripheral devices, and any other hardware components within a system. For example, communications fabric 1102 can be implemented with one or more buses or a cross switch. Memory 1106 and persistent storage 1108 are computer readable storage media. In this embodiment, memory 1106 includes random access memory (RAM). In general, memory 1106 can include any suitable volatile or non-volatile computer readable storage media. Cache 1116 is a fast memory that enhances the performance of computer processor(s) 1104 by holding recently accessed data, and data near accessed data, from memory 1106.

Program instructions and data (e.g., software and data) used to practice embodiments of the present invention may be stored in persistent storage 1108 and in memory 1106 for execution by one or more of the respective processor(s) 1104 via cache 1116. In an embodiment, persistent storage 1108 includes a magnetic hard disk drive. Alternatively, or in addition to a magnetic hard disk drive, persistent storage 1108 can include a solid-state hard drive, a semiconductor storage device, a read-only memory (ROM), an erasable programmable read-only memory (EPROM), a flash memory, or any other computer readable storage media that is capable of storing program instructions or digital information.

The media used by persistent storage 1108 may also be removable. For example, a removable hard drive may be used for persistent storage 1108. Other examples include optical and magnetic disks, thumb drives, and smart cards that are inserted into a drive for transfer onto another computer readable storage medium that is also part of persistent storage 1108. Software and data can be stored in persistent storage 1108 for access and/or execution by one or more of the respective processor(s) 1104 via cache 1116. With respect to user computing device 130, software and data includes user interface 132. With respect to server 120, software and data includes program 122.

Communications unit 1110, in these examples, provides for communications with other data processing systems or devices. In these examples, communications unit 1110 includes one or more network interface cards. Communications unit 1110 may provide communications through the use of either or both physical and wireless communications links. Program instructions and data (e.g., software and data) used to practice embodiments of the present invention may be downloaded to persistent storage 1108 through communications unit 1110.

I/O interface(s) 1112 allows for input and output of data with other devices that may be connected to each computer system. For example, I/O interface(s) 1112 may provide a connection to external device(s) 1118, such as a keyboard, a keypad, a touch screen, and/or some other suitable input device. External device(s) 1118 can also include portable computer readable storage media, such as, for example, thumb drives, portable optical or magnetic disks, and memory cards. Program instructions and data (e.g., software and data) used to practice embodiments of the present invention can be stored on such portable computer readable storage media and can be loaded onto persistent storage 1108 via I/O interface(s) 1112. I/O interface(s) 1112 also connect to display 1120.

Display 1120 provides a mechanism to display data to a user and may be, for example, a computer monitor.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

While particular embodiments of the present invention have been shown and described here, it will be understood to those skilled in the art that, based upon the teachings herein, changes and modifications may be made without departing from the embodiments and its broader aspects. Therefore, the appended claims are to encompass within their scope all such changes and modifications as are within the true spirit and scope of the embodiments. Furthermore, it is to be understood that the embodiments are solely defined by the appended claims. It will be understood by those with skill in the art that if a specific number of an introduced claim element is intended, such intent will be explicitly recited in the claim, and in the absence of such recitation no such limitation is present. For a non-limiting example, as an aid to understand, the following appended claims contain usage of the introductory phrases "at least one" and "one or more" to introduce claim elements. However, the use of such phrases should not be construed to imply that the introduction of a claim element by the indefinite articles "a" or "an" limits any particular claim containing such introduced claim element to embodiments containing only one such element, even when the same claim includes the introductory phrases "at least one" or "one or more" and indefinite articles such as "a" or "an", the same holds true for the use in the claims of definite articles.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart illustrations and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart illustrations and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart illustrations and/or block diagram block or blocks.

The flowchart illustrations and block diagrams in the Figures illustrate the architecture, functionality, and operation of possible implementations of systems, methods, and computer program products according to various embodiments of the present invention. In this regard, each block in the flowchart illustrations or block diagrams may represent a module, segment, or portion of instructions, which comprises one or more executable instructions for implementing the specified logical function(s). In some alternative implementations, the functions noted in the block may occur out of the order noted in the Figures. For example, two blocks shown in succession may, in fact, be executed substantially concurrently, or the blocks may sometimes be executed in the reverse order, depending upon the functionality involved. It will also be noted that each flowchart illustration and/or block of the block diagrams, and combinations of flowchart illustration and/or blocks in the block diagrams, can be implemented by special purpose hardware-based systems that perform the specified functions or acts or carry out combinations of special purpose hardware and computer instructions.

The descriptions of the various embodiments of the present invention have been presented for purposes of illustration but are not intended to be exhaustive or limited to the embodiments disclosed. Many modifications and variations will be apparent to those of ordinary skill in the art without departing from the scope and spirit of the invention. The terminology used herein was chosen to best explain the principles of the embodiment, the practical application or technical improvement over technologies found in the marketplace, or to enable others of ordinary skill in the art to understand the embodiments disclosed herein.

What is claimed is:

1. A computer-implemented method comprising:
   receiving, by one or more processors, a pair of documents from a user, wherein the pair of documents include a Scientific Drug Label and a Patient Drug Label, further comprising:
      converting, by the one or more processors, the pair of documents from a word format to a Portable Document Format (PDF);
      extracting, by the one or more processors, content from the PDF of the Scientific Drug Label in a structured format; and
      sorting, by the one or more processors, the extracted content into a corresponding section heading or a corresponding section subheading;
   converting, by the one or more processors, a complex medical language of the Scientific Drug Label into a simplified patient friendly language;
   analyzing, by the one or more processors, the simplified patient friendly language to identify one or more words, one or more phrases, or one or more sentences that have been modified, inserted, or deleted;
   responsive to determining the one or more words, the one or more phrases, or the one or more sentences are relevant to a patient, classifying, by the one or more processors, the one or more words, the one or more phrases, or the one or more sentences in one or more categories;
   searching, by the one or more processors, for a location in the Patient Drug Label that closely maps to the one or more words, the one or more phrases, or the one or more sentences to the Scientific Drug Label;
   incorporating, by the one or more processors, the one or more words, the one or more phrases, or the one or more sentences in a mapped location of the Patient Drug Label;
   outputting, by the one or more processors, an updated Patient Drug Label to the user;
   subsequent to outputting the updated Patient Drug Label to the user, requesting, by the one or more processors, feedback from the user;
   responsive to receiving the feedback from the user, validating, by the one or more processors, the feedback received from the user manually using a confidence score of one or more intermediate outputs; and
   annotating, by the one or more processors, the feedback received from the user.

2. The computer-implemented method of claim 1, wherein the one or more categories include a complete insertion of a sentence in the Scientific Drug Label, a complete deletion of the sentence in the Scientific Drug Label, and an insertion or a deletion of a word or a phrase in the Scientific Drug Label.

3. The computer-implemented method of claim 1, further comprising:
   subsequent to annotating the feedback received from the user, identifying, by the one or more processors, one or more engines to be retrained; and
   retraining, by the one or more processors, the one or more engines with the annotated feedback.

4. The computer-implemented method of claim 1, wherein the feedback received from the user includes an acceptance or a rejection of one or more changes incorporated into the updated Patient Drug Label.

5. The computer-implemented method of claim 1, further comprising:
   subsequent to sorting the extracted content into the corresponding section heading or the corresponding section subheading, extracting, by the one or more processors, one or more keywords and one or more key phrases from the extracted content using a custom-trained Spacey model to understand a concept of each sentence of the extracted content;
   mapping, by the one or more processors, one or more relationships between the Scientific Drug Label and the Patient Drug Label using a knowledge graph; and
   extracting, by the one or more processors, a confidence score for the one or more relationships mapped between the Scientific Drug Label and the Patient Drug Label.

6. The computer-implemented method of claim 5, wherein the one or more keywords and the one or more key phrases extracted from structured data includes a name of a drug, a composition of the drug, a shape of the drug, an appearance of the drug, a medical condition treated by the drug, a method to administer the drug, one or more side effects the patient may experience when taking the drug, and one or more precautions the patient should take when using the drug.

7. The computer-implemented method of claim 5, wherein extracting the one or more keywords and the one or more key phrases from the extracted content using the custom-trained Spacey model to understand the concept of each sentence of the extracted content further comprises:
   generating, by the one or more processors, a model for the one or more keywords and the one or more key phrases from the extracted content;
   determining, by the one or more processors, a position of the one or more keywords and the one or more key phrases from the extracted content;
   annotating, by the one or more processors, the position of the one or more keywords and the one or more key phrases from the extracted content; and
   training, by the one or more processors, on the annotated position of the one or more keywords and the one or more key phrases.

8. The computer-implemented method of claim 1, wherein incorporating the one or more words, the one or more phrases, or the one or more sentences in the mapped location of the Patient Drug Label further comprises:
   modifying, by the one or more processors, the one or more words, the one or more phrases, or the one or more sentences in the mapped location of the Patient Drug Label.

9. The computer-implemented method of claim 1, wherein incorporating the one or more words, the one or more phrases, or the one or more sentences in the mapped location of the Patient Drug Label further comprises:
   inserting, by the one or more processors, the one or more words, the one or more phrases, or the one or more sentences in the mapped location of the Patient Drug Label.

10. The computer-implemented method of claim 1, wherein incorporating the one or more words, the one or more phrases, or the one or more sentences in the mapped location of the Patient Drug Label further comprises:
    deleting, by the one or more processors, the one or more words, the one or more phrases, or the one or more sentences in the mapped location of the Patient Drug Label.

11. A computer program product comprising:
one or more computer readable storage media and program instructions stored on the one or more computer readable storage media, the program instructions comprising:
program instructions to receive a pair of documents from a user, wherein the pair of documents include a Scientific Drug Label and a Patient Drug Label, further comprising:
program instructions to convert the pair of documents from a word format to a Portable Document Format (PDF);
program instructions to extract content from the PDF of the Scientific Drug Label in a structured format; and
program instructions to sort the extracted content into a corresponding section heading or a corresponding section subheading;
program instructions to convert a complex medical language of the Scientific Drug Label into a simplified patient friendly language;
program instructions to analyze the simplified patient friendly language to identify one or more words, one or more phrases, or one or more sentences that have been modified, inserted, or deleted;
responsive to determining the one or more words, the one or more phrases, or the one or more sentences are relevant to a patient, program instructions to classify the one or more words, the one or more phrases, or the one or more sentences in one or more categories;
program instructions to search for a location in the Patient Drug Label that closely maps to the one or more words, the one or more phrases, or the one or more sentences to the Scientific Drug Label;
program instructions to incorporate the one or more words, the one or more phrases, or the one or more sentences in a mapped location of the Patient Drug Label;
program instructions to output an updated Patient Drug Label to the user;
responsive to receiving a feedback from the user, program instructions to validate, the feedback received from the user manually using a confidence score of one or more intermediate outputs; and
responsive to annotate the feedback received from the user.

12. The computer program product of claim 11, further comprising:
subsequent to sorting the extracted content into the corresponding section heading or the corresponding section subheading, program instructions to extract one or more keywords and one or more key phrases from the extracted content using a custom-trained Spacey model to understand a concept of each sentence of the extracted content;
program instructions to map one or more relationships between the Scientific Drug Label and the Patient Drug Label using a knowledge graph; and
program instructions to extract a confidence score for the one or more relationships mapped between the Scientific Drug Label and the Patient Drug Label.

13. The computer program product of claim 12, wherein extracting the one or more keywords and the one or more key phrases from the extracted content using the custom-trained Spacey model to understand the concept of each sentence of the extracted content further comprises:
program instructions to generate a model for the one or more keywords and the one or more key phrases from the extracted content;
program instructions to determine a position of the one or more keywords and the one or more key phrases from the extracted content;
program instructions to annotate the position of the one or more keywords and the one or more key phrases from the extracted content; and
program instructions to train on the annotated position of the one or more keywords and the one or more key phrases.

14. A computer system comprising:
one or more computer processors;
one or more computer readable storage media;
program instructions collectively stored on the one or more computer readable storage media for execution by at least one of the one or more computer processors, the stored program instructions comprising:
one or more computer readable storage media and program instructions stored on the one or more computer readable storage media, the program instructions comprising:
program instructions to receive a pair of documents from a user, wherein the pair of documents include a Scientific Drug Label and a Patient Drug Label, further comprising:
program instructions to convert the pair of documents from a word format to a Portable Document Format (PDF);
program instructions to extract content from the PDF of the Scientific Drug Label in a structured format; and
program instructions to sort the extracted content into a corresponding section heading or a corresponding section subheading;
program instructions to convert a complex medical language of the Scientific Drug Label into a simplified patient friendly language;
program instructions to analyze the simplified patient friendly language to identify one or more words, one or more phrases, or one or more sentences that have been modified, inserted, or deleted;
responsive to determining the one or more words, the one or more phrases, or the one or more sentences are relevant to a patient, program instructions to classify the one or more words, the one or more phrases, or the one or more sentences in one or more categories;
program instructions to search for a location in the Patient Drug Label that closely maps to the one or more words, the one or more phrases, or the one or more sentences to the Scientific Drug Label;
program instructions to incorporate the one or more words, the one or more phrases, or the one or more sentences in a mapped location of the Patient Drug Label;
program instructions to output an updated Patient Drug Label to the user;
responsive to receiving a feedback from the user, program instructions to validate, the feedback received from the user manually using a confidence score of one or more intermediate outputs; and
responsive to annotate the feedback received from the user.

15. The computer system of claim 14, further comprising:
subsequent to sorting the extracted content into the corresponding section heading or the corresponding section subheading, program instructions to extract one or more keywords and one or more key phrases from the extracted content using a custom-trained Spacey model to understand a concept of each sentence of the extracted content;
program instructions to map one or more relationships between the Scientific Drug Label and the Patient Drug Label using a knowledge graph; and
program instructions to extract a confidence score for the one or more relationships mapped between the Scientific Drug Label and the Patient Drug Label.

16. The computer system of claim 15, wherein extracting the one or more keywords and the one or more key phrases from the extracted content using the custom-trained Spacey model to understand the concept of each sentence of the extracted content further comprises:
program instructions to generate a model for the one or more keywords and the one or more key phrases from the extracted content;
program instructions to determine a position of the one or more keywords and the one or more key phrases from the extracted content;
program instructions to annotate the position of the one or more keywords and the one or more key phrases from the extracted content; and
program instructions to train on the annotated position of the one or more keywords and the one or more key phrases.

* * * * *